(12) United States Patent
Chen et al.

(10) Patent No.: US 8,777,965 B2
(45) Date of Patent: Jul. 15, 2014

(54) DEVICES AND METHODS FOR LAPAROSCOPIC HERNIA REPAIR

(75) Inventors: Eugene G. Chen, Carlsbad, CA (US); Tracy D. Maahs, Yorba Linda, CA (US); Richard C. Ewers, Fullerton, CA (US); Lee L. Swanstrom, Portland, OR (US)

(73) Assignee: USGI Medical, Inc., San Clemente, CA (US)

( * ) Notice: Subject to any disclaimer, the term of this patent is extended or adjusted under 35 U.S.C. 154(b) by 283 days.

(21) Appl. No.: 13/103,936

(22) Filed: May 9, 2011

(65) Prior Publication Data

US 2012/0265218 A1 Oct. 18, 2012

Related U.S. Application Data

(60) Provisional application No. 61/476,129, filed on Apr. 15, 2011.

(51) Int. Cl.
*A61B 17/04* (2006.01)
*A61B 17/00* (2006.01)

(52) U.S. Cl.
CPC ......... *A61B 17/0401* (2013.01); *A61B 17/0487* (2013.01); *A61B 17/0057* (2013.01); *A61B 2017/0462* (2013.01); *A61B 17/0469* (2013.01); *A61B 2017/00575* (2013.01); *A61B 2017/00637* (2013.01)
USPC ............................ 606/139; 606/151; 606/232

(58) Field of Classification Search
USPC ................. 606/139, 142, 143, 151, 213–215
See application file for complete search history.

(56) References Cited

U.S. PATENT DOCUMENTS

| | | | | |
|---|---|---|---|---|
| 4,006,747 A | * | 2/1977 | Kronenthal et al. | 606/144 |
| 4,235,238 A | * | 11/1980 | Ogiu et al. | 606/145 |
| 5,041,129 A | * | 8/1991 | Hayhurst et al. | 606/232 |
| 5,254,126 A | * | 10/1993 | Filipi et al. | 606/146 |
| 5,269,809 A | * | 12/1993 | Hayhurst et al. | 606/232 |
| 5,464,426 A | * | 11/1995 | Bonutti | 606/232 |
| 5,507,755 A | * | 4/1996 | Gresl et al. | 606/139 |
| 5,618,290 A | * | 4/1997 | Toy et al. | 606/139 |
| 6,113,611 A | * | 9/2000 | Allen et al. | 606/151 |
| 6,152,935 A | * | 11/2000 | Kammerer et al. | 606/144 |
| 7,186,262 B2 | | 3/2007 | Saadat | |
| 7,347,863 B2 | * | 3/2008 | Rothe et al. | 606/139 |
| 7,601,159 B2 | * | 10/2009 | Ewers et al. | 606/139 |
| 7,618,426 B2 | | 11/2009 | Ewers et al. | |
| 7,621,925 B2 | | 11/2009 | Saadat et al. | |
| 7,736,374 B2 | | 6/2010 | Vaughan et al. | |
| 7,736,378 B2 | | 6/2010 | Maahs et al. | |
| 7,736,379 B2 | | 6/2010 | Ewers et al. | |
| 7,846,180 B2 | * | 12/2010 | Cerier | 606/232 |
| 7,909,851 B2 | * | 3/2011 | Stone et al. | 606/232 |
| 7,942,898 B2 | | 5/2011 | Ewers et al. | |
| 8,034,076 B2 | * | 10/2011 | Criscuolo et al. | 606/219 |
| 8,057,490 B2 | * | 11/2011 | Harris et al. | 606/139 |

(Continued)

*Primary Examiner* — Melanie Tyson
*Assistant Examiner* — Todd J Scherbel
(74) *Attorney, Agent, or Firm* — Kenneth H. Ohriner; Perkins Coie LLP

(57) ABSTRACT

Devices and methods for laparoscopically repairing a hernia are described. In some embodiments, a laparoscopic instrument is used to deploy one or more tissue anchor assemblies into the edges of the fascia tissue surrounding or adjacent to the hernia defect. The tissue anchor assemblies are used to cause the fascia tissue to be approximated to facilitate the repair procedure, to improve healing, and to reduce the incidence of recurrence.

11 Claims, 25 Drawing Sheets

(56) References Cited

U.S. PATENT DOCUMENTS

| | | | |
|---|---|---|---|
| 8,257,394 B2* | 9/2012 | Saadat et al. | 606/232 |
| 8,343,231 B1* | 1/2013 | Christoudias | 623/23.72 |
| 8,357,172 B2* | 1/2013 | Harper | 606/151 |
| 2003/0171761 A1* | 9/2003 | Sancoff et al. | 606/139 |
| 2004/0092969 A1* | 5/2004 | Kumar | 606/151 |
| 2004/0122456 A1 | 6/2004 | Saadat et al. | |
| 2005/0216040 A1* | 9/2005 | Gertner et al. | 606/151 |
| 2005/0216042 A1* | 9/2005 | Gertner | 606/151 |
| 2005/0251157 A1 | 11/2005 | Saadat et al. | |
| 2005/0251207 A1 | 11/2005 | Flores et al. | |
| 2006/0235446 A1* | 10/2006 | Godin | 606/151 |
| 2007/0027358 A1* | 2/2007 | Gertner et al. | 600/37 |
| 2007/0112338 A1* | 5/2007 | Cohen et al. | 606/1 |
| 2008/0009888 A1 | 1/2008 | Ewers et al. | |
| 2008/0132948 A1* | 6/2008 | Surti et al. | 606/232 |
| 2008/0319455 A1* | 12/2008 | Harris et al. | 606/139 |
| 2009/0018576 A1* | 1/2009 | Binmoeller | 606/215 |
| 2009/0312603 A1 | 12/2009 | Lam et al. | |
| 2011/0208209 A1* | 8/2011 | Ewers et al. | 606/139 |

* cited by examiner

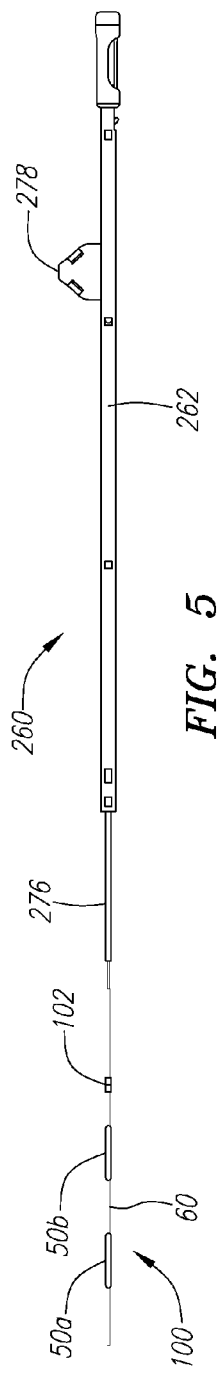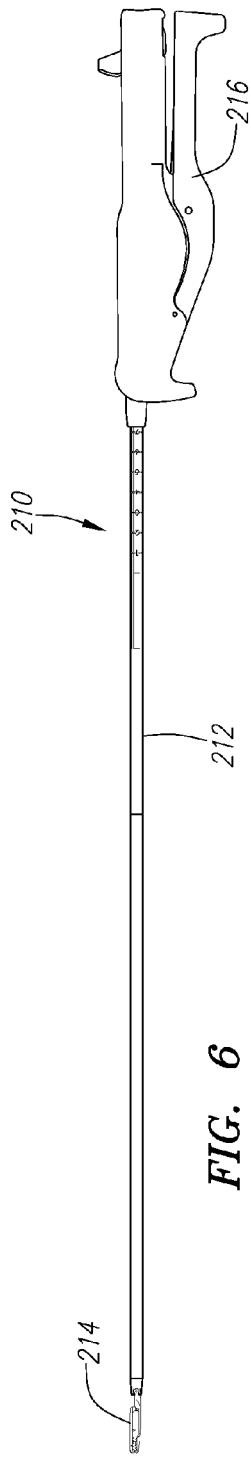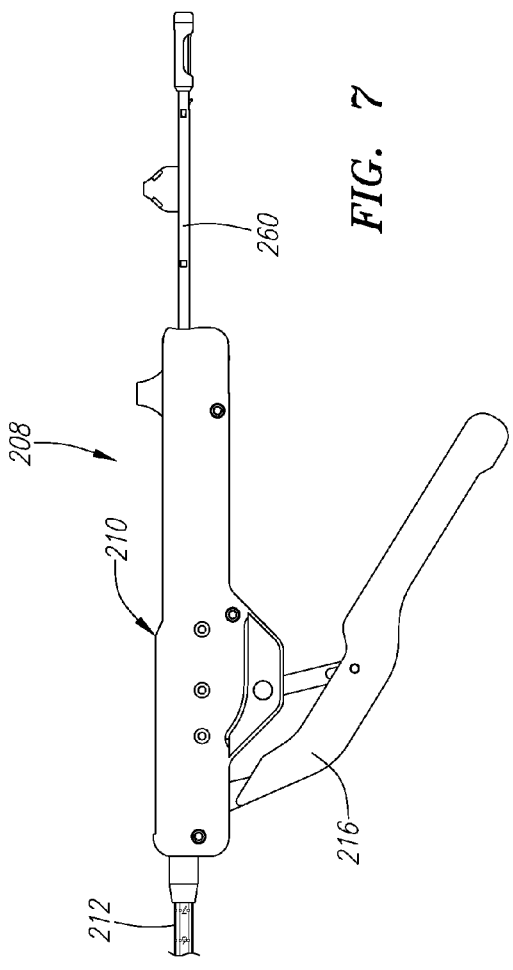

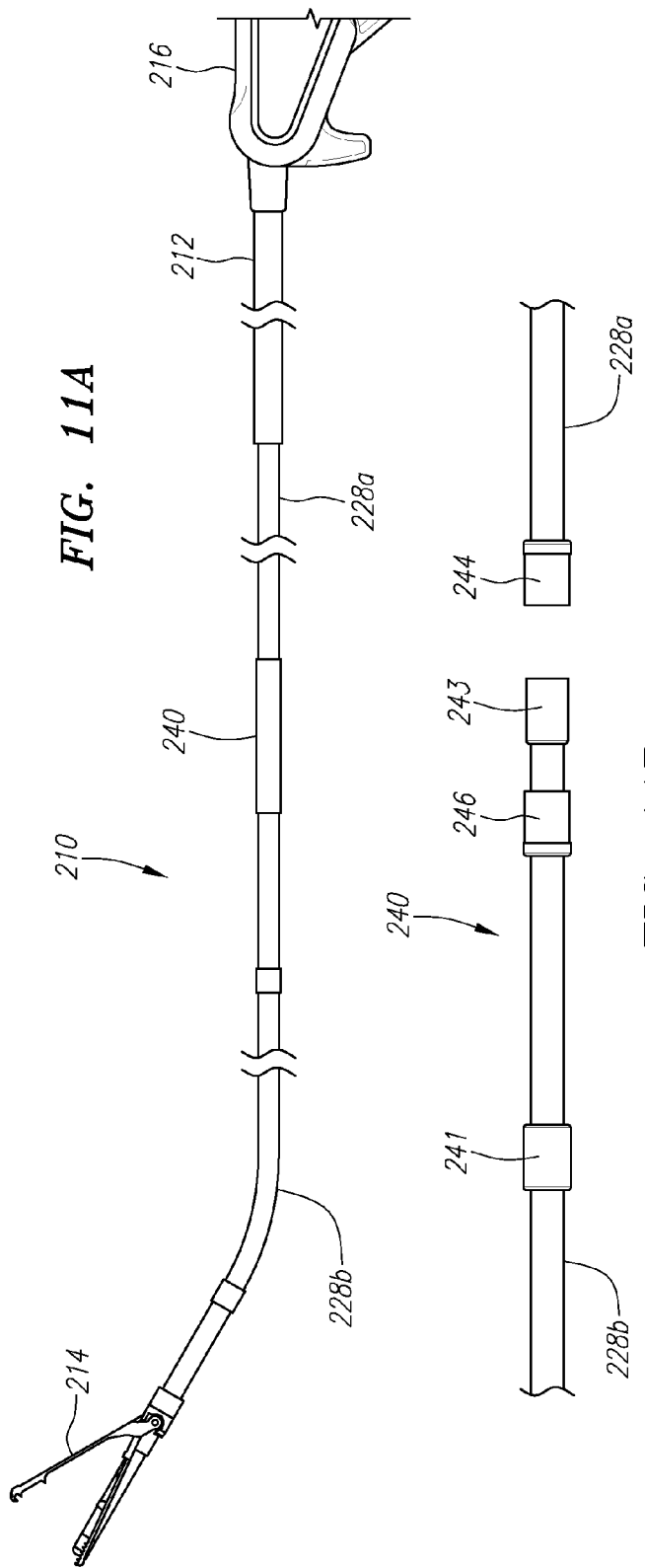

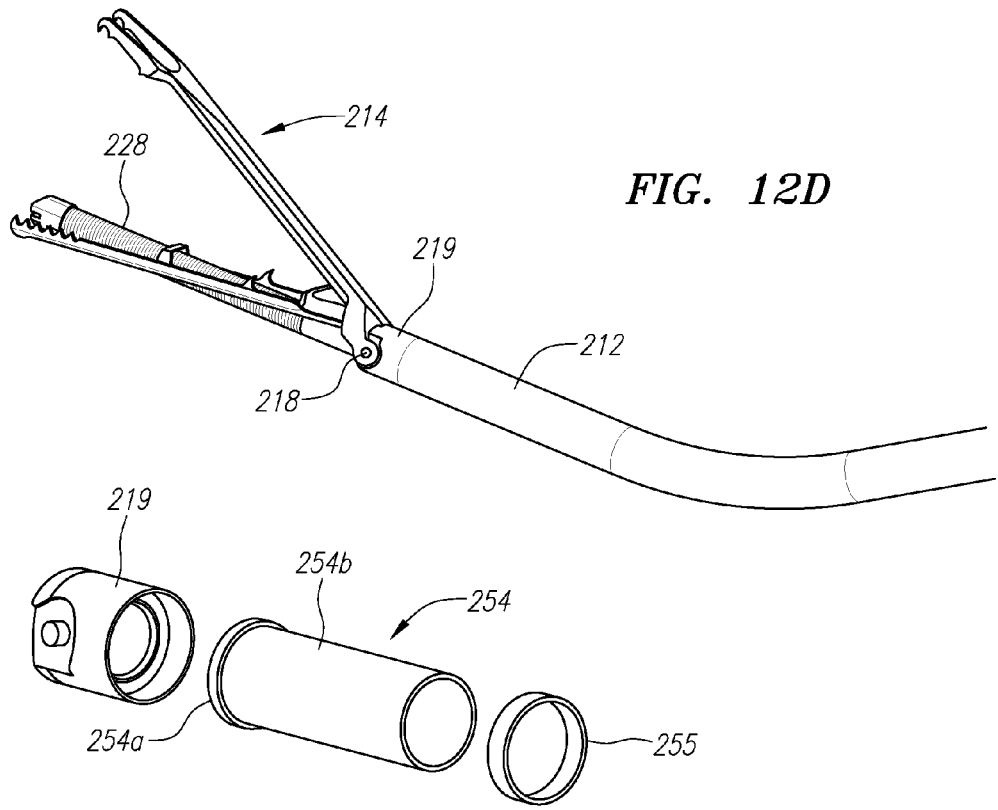
FIG. 12D
FIG. 12E
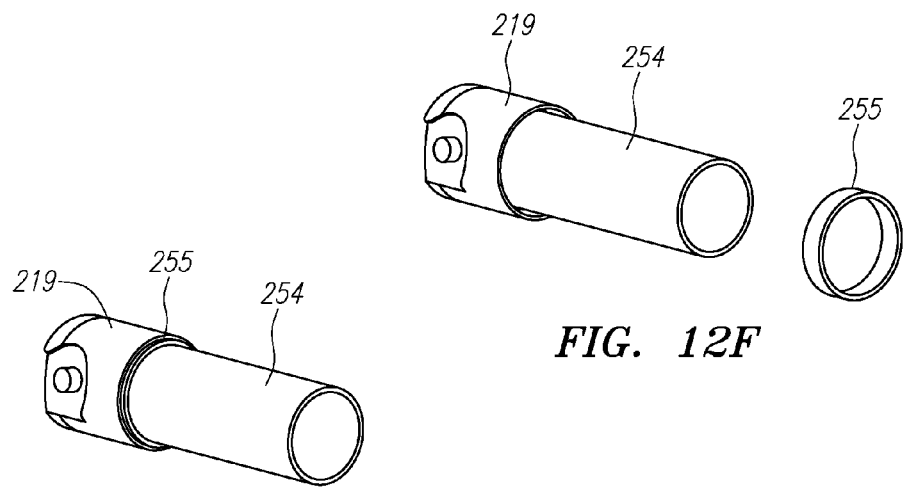
FIG. 12F
FIG. 12G

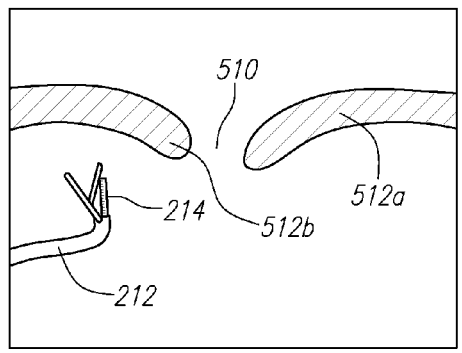
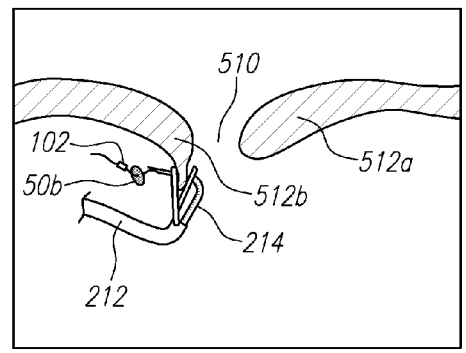
*FIG. 28A*  *FIG. 28B*
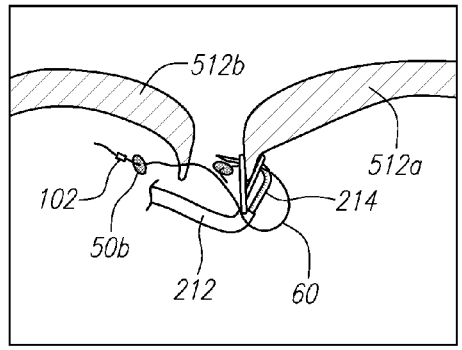
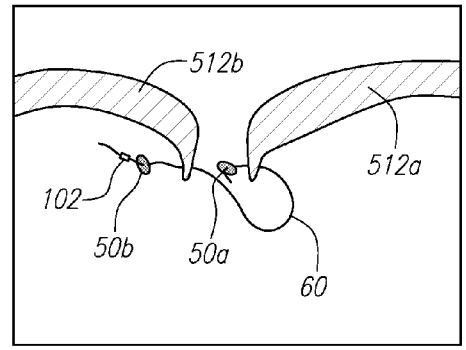
*FIG. 28C*  *FIG. 28D*
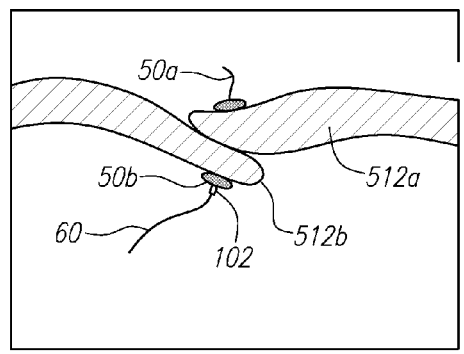
*FIG. 28E*

DEVICES AND METHODS FOR LAPAROSCOPIC HERNIA REPAIR

CROSS-REFERENCE TO RELATED APPLICATIONS

This application claims the benefit of priority to U.S. Provisional Patent Application No. 61/476,129, filed on Apr. 15, 2011, the contents of which are incorporated herein by reference in their entirety. This application also relates to U.S. Provisional Patent Application Ser. No. 61/307,376, filed on Feb. 23, 2010, and U.S. patent application Ser. No. 13/033,485, filed on Feb. 23, 2011, the contents of each of which are incorporated herein by reference in their entireties.

BACKGROUND

A hernia is the protrusion of an organ or the fascia of an organ through the wall of the cavity that normally contains it. By far the most common hernias (up to 75% of all abdominal hernias) are the so-called inguinal hernias. Inguinal hernias are further divided into the more common indirect inguinal hernia, in which the inguinal canal is entered via a congenital weakness at its entrance (the internal inguinal ring), and the direct inguinal hernia type, where the hernia contents push through a weak spot in the back wall of the inguinal canal.

Femoral hernias occur just below the inguinal ligament, when abdominal contents pass into the weak area at the posterior wall of the femoral canal. They can be hard to distinguish from the inguinal type (especially when ascending cephalad): however, they generally appear more rounded, and, in contrast to inguinal hernias, there is a strong female preponderance in femoral hernias.

Higher in the abdomen, an (internal) "diaphragmatic hernia" results when part of the stomach or intestine protrudes into the chest cavity through a defect in the diaphragm. A hiatus hernia is a particular variant of this type, in which the normal passageway through which the esophagus meets the stomach (esophageal hiatus) serves as a functional "defect", allowing part of the stomach to (periodically) "herniate" into the chest. Hiatus hernias may be either "sliding," in which the gastroesophageal junction itself slides through the defect into the chest, or non-sliding (also known as para-esophageal), in which case the junction remains fixed while another portion of the stomach moves up through the defect. Non-sliding or para-esophageal hernias can be dangerous as they may allow the stomach to rotate and obstruct.

An incisional hernia can develop in the scar tissue around any surgery performed in the abdominal area, from the breastbone down to the groin. Depending upon the location of the hernia, internal organs may press through the weakened abdominal wall. The rate of incisional hernia occurrence can be as high as 13% with some abdominal surgeries. These hernias may occur after large surgeries such as intestinal or vascular (heart, arteries, and veins) surgery, or after smaller surgeries such as an appendectomy or a laparoscopy, which typically requires a small incision at the navel. Incisional hernias themselves can be very small or large and complex, involving growth along the scar tissue of a large incision. They may develop months after the surgery or years after, usually because of inadequate healing or excessive pressure on an abdominal wall scar. The factors that increase the risk of incisional hernia are conditions that increase strain on the abdominal wall, such as, obesity, advanced age, malnutrition, poor metabolism (digestion and assimilation of essential nutrients), pregnancy, dialysis, excess fluid retention, and either infection or hematoma (bleeding under the skin) after a prior surgery.

Many procedures for hernia repair involve the permanent placement of surgical (prosthetic) mesh patches well beyond the edges of the weakened area or defect in the abdominal wall. The mesh is sewn or tacked to the area, bridging the hole or weakened area. As the area heals, the mesh is intended to become firmly integrated into the inner abdominal wall membrane (peritoneum) that protects the organs of the abdomen. Autogenous tissue (skin from the patient's own body) has also been used for this type of repair.

Two surgical approaches are used to treat incisional hernias: either a laparoscopic incisional herniorrhaphy, which uses small incisions and a laparoscope; or a conventional open repair procedure, which accesses the hernia through a larger abdominal incision. Open procedures may be necessary if the intestines have become trapped in the hernia (incarceration) or the trapped intestine has become twisted and its blood supply cut off (strangulation). Extremely obese patients may also require an open procedure because deeper layers of fatty tissue will have to be removed from the abdominal wall. Mesh may be used with both types of surgical access.

In both open and laparoscopic procedures, the patient lies on the operating table, either flat on the back or on the side, depending on the location of the hernia. General anesthesia is usually given, though some patients may have local or regional anesthesia, depending on the location of the hernia and complexity of the repair. A catheter may be inserted into the bladder to remove urine and decompress the bladder. If the hernia is near the stomach, a gastric (nose or mouth to stomach) tube may be inserted to decompress the stomach.

In an open procedure, an incision is made just large enough to remove fat and scar tissue from the abdominal wall near the hernia. The outside edges of the weakened hernial area are defined and excess tissue removed from within the area. Mesh is then applied so that it overlaps the weakened area by several inches (centimeters) in all directions. Non-absorbable sutures are placed into the full thickness of the abdominal wall. The sutures are tied down and knotted.

In the less-invasive laparoscopic procedure, multiple small incisions will be made to access the hernia site—the laparoscope is inserted in one incision and surgical instruments in the others to remove tissue and place the mesh in the same fashion as in an open procedure. Significantly less abdominal wall tissue is removed in laparoscopic repair. The surgeon views the entire procedure on a video monitor to guide the placement and attachment of the mesh.

Patients will usually go home the day of surgery and can expect a one- to two-week recovery period at home, and then a return to normal activities. Although good outcomes are expected with incisional hernia repair, particularly with the laparoscopic method, recurrence rates after the first repair of an incisional hernia can range from 25-52%.

SUMMARY

In a first aspect, laparoscopic hernia repair includes a number of methods and devices. The devices are introduced laparoscopically (e.g., via one or more trocars, etc.) into the patient's body and into the peritoneal cavity to approach the weakened area or defect in the fascia. Once the instruments are positioned near the hernia defect, the edges of the fascia surrounding the defect are temporarily engaged and/or grasped and the engaged tissue is manipulated by a surgeon or practitioner from outside the patient's body. One or more tissue fasteners, such as one or more tissue anchor assemblies each including a pair of anchors connected to each other by a suture, are deployed across the hernia defect. The pair of anchors or other tissue fasteners are approximated and secured, thereby bringing the edges of the fascia surrounding the defect relatively closer to one another. In some embodiments, the fascia edges are brought into side-by-side or overlapping contact with one another. In some embodiments, a surgical mesh is then deployed laparoscopically across the defect.

In engaging, manipulating, and/or securing the tissue, various methods and devices may be implemented. For instance, a tissue securement device may be delivered and positioned through the abdominal wall via one or more trocars. In some embodiments, the tissue securement device includes an end effector suitable for contacting the edges of the fascia surrounding the hernia defect, manipulating the fascia tissue, and/or deploying one or more tissue anchors through the fascia. The tissue anchor(s) extending on a connecting member (e.g., a suturing element) may be disposed through opposed edges of the fascia. A tissue manipulation assembly positioned at the distal end of a tissue securement device may be used for engaging the fascia tissue and deploying the tissue anchor to secure the tissue with the tissue anchor. A second tissue anchor may then be deployed in a second region of the fascia, after which the fascia tissue regions are brought into apposition by decreasing the length of the connecting member extending between the two tissue anchors. In some embodiments, this is done by advancing an uni-directional cinching element or other locking mechanism along the connecting member. In some embodiments, the foregoing method is repeated at a plurality of locations along the length of the hernia defect.

In some embodiments, the laparoscopic hernia repair method includes at least the following steps:
   laparoscopically introducing a tissue approximation device into the peritoneal cavity and into the vicinity of a hernia defect;
   approximating a first region of tissue at or near a first edge of the hernia defect and a second region of tissue at or near a second edge of the hernia defect with the tissue approximation device; and
   securing the approximated first and second regions of tissue with a first tissue fastener.
Some examples of the foregoing hernia repair method include one or more of the following additional steps:
   securing the approximated first and second regions of tissue with a plurality of additional tissue fasteners;
   oversewing the approximated first and second regions of tissue after securing the first and second regions of tissue;
   applying a surgical mesh over the approximated first and second regions of tissue and securing the surgical mesh to tissue in the vicinity of the first and second regions of tissue.
In other embodiments, the laparoscopic hernia repair method includes the steps of:
   laparoscopically introducing a tissue fastener into the peritoneal cavity and into the vicinity of a hernia defect;
   deploying a first portion of the tissue fastener into or through a first region of tissue at or near a first edge of the hernia defect;
   deploying a second portion of the tissue fastener into or through a second region of tissue at or near a second edge of the hernia defect; and
   approximating the first and second portions of the tissue fastener to thereby approximate the first and second regions of tissue.
Some examples of the foregoing hernia repair method include one or more of the following additional steps:
   deploying a plurality of additional tissue fasteners into or through the first and second regions of tissue;
   oversewing the approximated first and second regions of tissue after approximating the first and second regions of tissue;
   applying a surgical mesh over the approximated first and second regions of tissue and securing the surgical mesh to tissue in the vicinity of the first and second regions of tissue.

In some embodiments, each of the foregoing embodiments of the laparoscopic hernia repair method is performed using a tissue fastener that includes a tissue anchor assembly having first and second tissue anchors and a locking mechanism retained on a connecting member, such as a suture. In some embodiments, at least one of the tissue anchors and the locking mechanism are movable on the connecting member, thereby facilitating approximation of the tissue anchors along the connecting member.

BRIEF DESCRIPTION OF THE DRAWINGS

FIG. 5 is a side view of a third embodiment of an anchor deployment catheter.

FIG. 6 is a side view of a laparoscopic tissue manipulation and anchor deployment device.

FIG. 7 is a side view of a first embodiment of a handle portion of the laparoscopic tissue manipulation and anchor deployment device of FIG. 6.

FIG. 11A is a side view of another embodiment of a laparoscopic tissue manipulation and anchor deployment device.

FIG. 11B is a side view of a portion of a spring-loaded variable spacer of the laparoscopic tissue manipulation and anchor deployment device shown in FIG. 11A, shown with the spring and piston sleeve removed for clarity.

FIG. 11C is a side view of a spring-loaded variable spacer of the laparoscopic tissue manipulation and anchor deployment device shown in FIG. 11A.

FIG. 12D is a side view of a distal end effector of the laparoscopic tissue manipulation and anchor deployment device shown in FIG. 12A.

FIGS. 12E-G are perspective views of a rotatable connection between the distal end effector and the tubular body of the laparoscopic tissue manipulation and anchor deployment device shown in FIG. 12A.

FIGS. 28A-E are cross-sectional views showing the progression of a portion of a laparoscopic hernia repair procedure.

DETAILED DESCRIPTION

Figure 1:
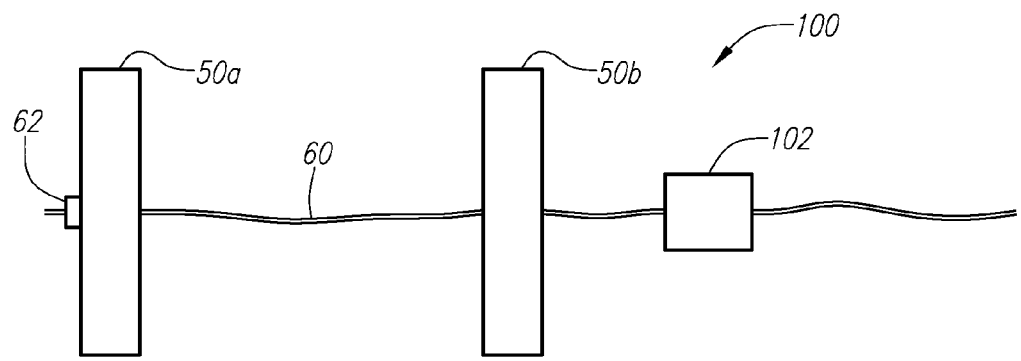
FIG. 1 is a schematic representation of a tissue anchor assembly.

Laparoscopic surgical devices and methods for engaging, manipulating, reconfiguring, and securing tissue are described herein. In several embodiments, the methods entail performing surgery through one or a limited number of trocars, eliminating the need for an open surgical procedure. Laparoscopic procedures provide faster healing times, less scarring, and less pain which could lead to reduced hospitalization and quicker recovery in comparison to most open surgical procedures.

In several embodiments, the laparoscopic surgical procedures are performed using devices that have been developed by USGI Medical, Inc. of San Clemente, Calif. Several tissue manipulation and tissue anchor delivery devices are described in the following United States patent applications:

TABLE 2

| U.S. patent application Ser. No. | Filing Date |
| --- | --- |
| 10/612,109 | Jul. 1, 2003 |
| 10/639,162 | Aug. 11, 2003 |
| 10/672,375 | Sept. 26, 2003 |
| 10/734,547 | Dec. 12, 2003 |
| 10/734,562 | Dec. 12, 2003 |
| 10/735,030 | Dec. 12, 2003 |
| 10/840,950 | May 7, 2004 |
| 10/955,245 | Sept. 29, 2004 |
| 11/070,863 | Mar. 1, 2005 |
| 12/486,578 | Jun. 17, 2009 |

The foregoing applications describe several tissue manipulation and tissue anchor delivery devices and embodiments, including flexible devices used for endolumenal procedures. Several tissue anchor delivery devices suitable for laparoscopic use are described more fully below.

Endolumenal tissue grasping devices are described in several of the United States patent applications listed above, and in the following United States patent applications:

TABLE 3

| U.S. patent application Ser. No. | Filing Date |
| --- | --- |
| 11/736,539 | Apr. 17, 2007 |
| 11/736,541 | Apr. 17, 2007 |

Tissue anchors are described in several of the United States patent applications listed above, and in the following United States patent applications:

TABLE 4

| U.S. patent application Ser. No. | Filing Date |
| --- | --- |
| 10/612,170 | Jul. 1, 2003 |
| 10/841,411 | May 7, 2004 |
| 11/404,423 | Apr. 14, 2006 |
| 11/773,933 | Jul. 5, 2007 |

Each of the foregoing patent applications is hereby incorporated by reference in its entirety.

Tissue Anchors and Delivery Devices and Methods

Several embodiments of the laparoscopic surgical procedures described herein include the steps of acquiring (e.g., by grasping) a first region of tissue, deploying or implanting a first fastener (e.g., a first tissue anchor of a tissue anchor assembly) into or through the first region of tissue, acquiring (e.g., by grasping) a second region of tissue, deploying or implanting a second fastener (e.g., a second tissue anchor of a tissue anchor assembly) into or through the second region of tissue, then approximating the first and second fasteners to cause the first and second tissue regions to be brought into proximity relative to one another. For simplicity, the discussion herein will describe tissue anchor assemblies holding regions of tissue comprising or adjacent to an incisional/ventral hernia, with it being understood that regions of tissue associated with other types of hernias or portions or sections of tissue in other regions of the body of a patient are suitably retained by the tissue anchor assemblies and other fasteners described herein. The following sections include descriptions of several embodiments of devices that are suitable for performing these and other laparoscopic surgical procedures.

In several embodiments, a plurality of tissue anchor assemblies are used to approximate regions of tissue on opposed sides of an incisional/ventral or other type of hernia. In some embodiments, the tissue anchor assemblies include tissue anchors such as those described in several of the United States patent applications incorporated by reference above, including Ser. Nos. 10/612,170, 10/841,411, 11/404,423, and 11/773,933. In other embodiments, the tissue anchor assemblies include "T"-anchors, basket anchors, and other types of anchors known to those skilled in the art. A schematic representation of a suitable tissue anchor assembly is shown in FIG. 1. In still other embodiments, regions of tissue are approximated using staples, tacks, clips, rivets, sutures, "H"-fasteners, "T"-tags, barbed or quilled suture, combinations of the foregoing, and/or other types of fasteners known to those skilled in the art. For clarity, the descriptions contained in this disclosure will focus on tissue anchors and tissue anchor assemblies, with the understanding that the methods and processes described herein are not intended to be limited to tissue anchor assemblies unless otherwise stated.

Figure 2A:
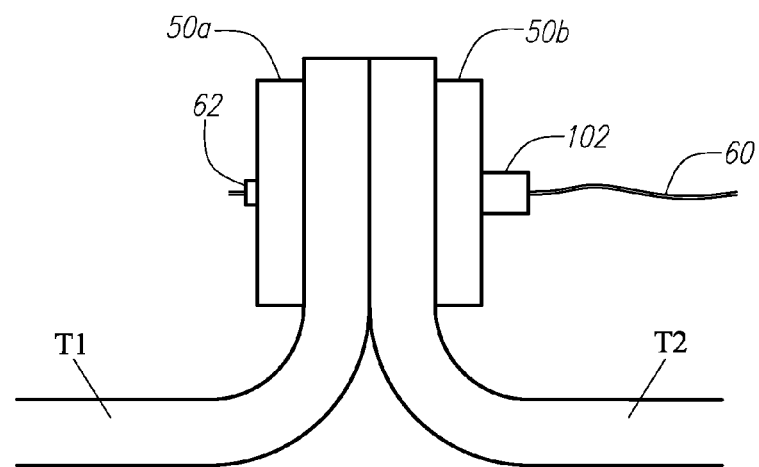
FIGS. 2A and 2B are schematic representations of a tissue anchor assembly securing a pair of tissue regions.
Figure 2B:
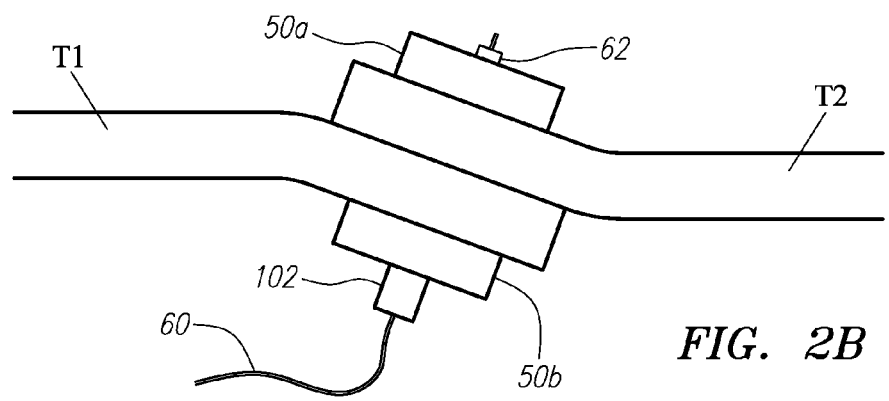

In some embodiments, the tissue anchor assemblies include a pair of tissue anchors 50a, 50b slidably retained by a connecting member, such as a suture 60. The suture 60 may be formed of conventional materials, such as polyglycolic acid, polylactic acid, polydioxanone, nylon, polypropylene. In other embodiments, the connecting member or suture 60 is formed of stainless steel, Nitinol, or other suitable material. In other embodiments, one or both of the tissue anchors 50a, 50b are retained at a fixed location on the connecting member. In still other embodiments, each of the tissue anchors is retained on a separate suture 60 and the separate sutures are connected together by tying, knotting, locking, or other securement mechanism. In the FIG. 1 embodiment, a locking mechanism, such as a cinch 102, is also slidably retained on the suture 60. The cinch 102 is configured to be slidable on the suture 60 in only a single direction (one-way or uni-directional), in particular, toward the distal end of the suture. Several types of cinches and other locking mechanisms—and their structures and modes of operation—are described in several of the United States Patent Applications incorporated by reference above, including Ser. Nos. 10/612,170, 10/612,491, 10/841, 411, 11/404,423, and 11/773,933. The cinch 102 or other locking mechanism is configured to provide a cinching force against the anchors 50a, 50b in order to impart a tension force on the suture. Accordingly, the tissue anchor assembly 100 is adapted to hold two regions of tissue together or in proximity to one another, as shown in FIGS. 2A and 2B. In addition, as described below, the position of the cinch 102 or other locking mechanism on the suture 60 is able to be adjusted by the user during deployment of the tissue anchor assembly, thereby allowing the user to adjust the amount of tension force applied to the suture 60, and the amount of force that the anchors 50a, 50b impart to the regions of tissue T1, T2.

The tissue anchor assembly 100 may be used to maintain regions of tissue in at least two relative orientations. In a first orientation (referred to herein as a "side-by-side" orientation), shown in FIG. 2A, a first tissue region T1 is secured to a second region of tissue T2 by causing the ends of the tissue regions to be brought substantially together and the anchor assembly 100 or other tissue fastener is deployed through both tissue regions T1, T2 such that both tissue anchors 50a, 50b of the tissue anchor assembly 100 or other tissue fastener remain on the same side (e.g., the upper side as shown in FIG. 2A) of the two regions of tissue T1, T2 after they are brought substantially together. In a second orientation (referred to herein as an "overlapping" orientation), shown in FIG. 2B, a first tissue region T1 is secured to a second tissue region T2 by causing the ends of the tissue regions to be overlapped and the anchor assembly 100 or other tissue fastener deployed through both tissue regions T1, T2 such that a first tissue anchor 50a is located on a first side (e.g., the upper side as shown in FIG. 2B) of the two regions of tissue T1, T2 and a second tissue anchor 50b is located on a second side (e.g., the lower side as shown in FIG. 2B) of the two regions of tissue T1, T2 after they are brought substantially together. As described below, a surgeon or other user deploying tissue anchor assemblies 100 or other tissue fasteners may select one of the foregoing orientations, or another orientation, in order to secure tissue regions in a particular manner or to achieve another desired result.

In several embodiments, a delivery device is used to deploy the tissue anchors and tissue anchor assemblies 100 or other tissue fasteners laparoscopically. An example of a suitable delivery device is shown in FIGS. 3-8. Embodiments of the device shown in FIGS. 3-8 but having a flexible shaft for use in endolumenal procedures are described in substantial detail in U.S. patent application Ser. No. 12/486,578, which is hereby incorporated by reference in its entirety (including all references cited therein) as if fully set forth herein. The laparoscopic embodiment of the delivery device 208 is described briefly below. In other embodiments, one or more tissue fasteners are deployed using one or more delivery/deployment devices suitable for deploying the particular type of tissue fastener desired (e.g., staplers, clip appliers, tack or rivet deployment devices, other types of anchor deployment devices, and the like). In still other embodiments, a tissue fastener deployment device includes or is used in combination with a device used to approximate two or more regions of tissue. For clarity, the descriptions contained in this disclosure will focus on the tissue anchor delivery device shown in FIGS. 3-8, with the understanding that the methods and processes described herein are not intended to be limited to these delivery devices unless otherwise stated.

Figure 8:
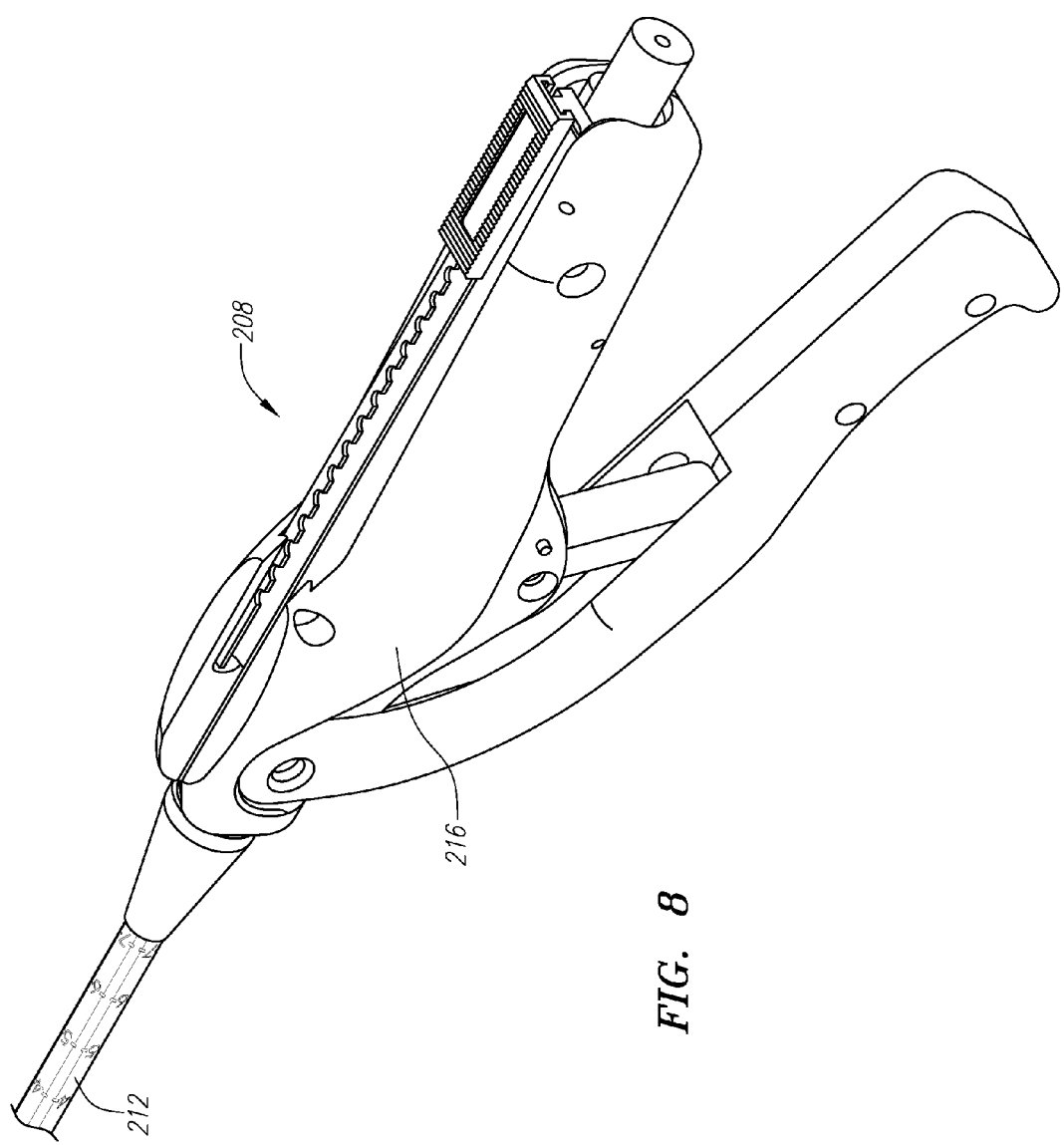
FIG. 8 is a perspective view of second embodiment of a handle portion of the laparoscopic tissue manipulation and anchor deployment device of FIG. 6.

Turning to the device shown in FIGS. 6-8, in manipulating tissue or creating tissue folds, a device having a handle 216, a substantially rigid shaft 212, and a distal end effector 214 is advanced laparoscopically, e.g., via a trocar, etc., into the patient's body, e.g., through the abdominal wall and into the peritoneal cavity. The end effector 214 is moved to the site of the target tissue, e.g., the location of a ventral hernia. The target tissue may be engaged or grasped and the engaged tissue may be manipulated by a surgeon or practitioner from outside the patient's body. Examples of grasping and manipulating target tissue are described in further detail in the '578 application incorporated by reference above, as well as in U.S. patent application Ser. No. 10/955,245, filed Sep. 29, 2004, which is also incorporated herein by reference, as well as U.S. patent application Ser. No. 10/735,030, filed Dec. 12, 2003, which is also incorporated herein by reference in its entirety.

Figure 3:
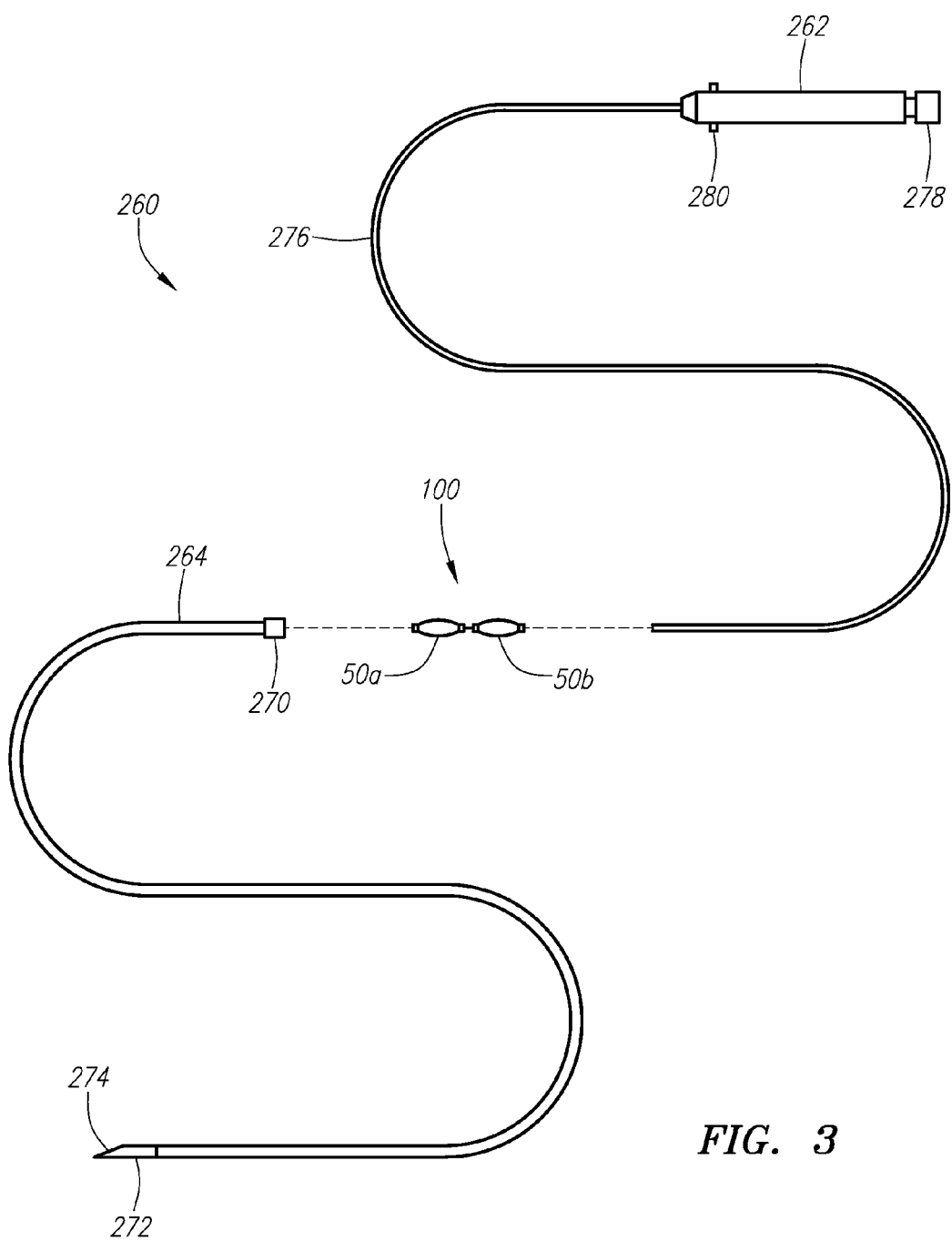
FIG. 3 is an exploded view of a first embodiment of an anchor deployment catheter.
Figure 4:
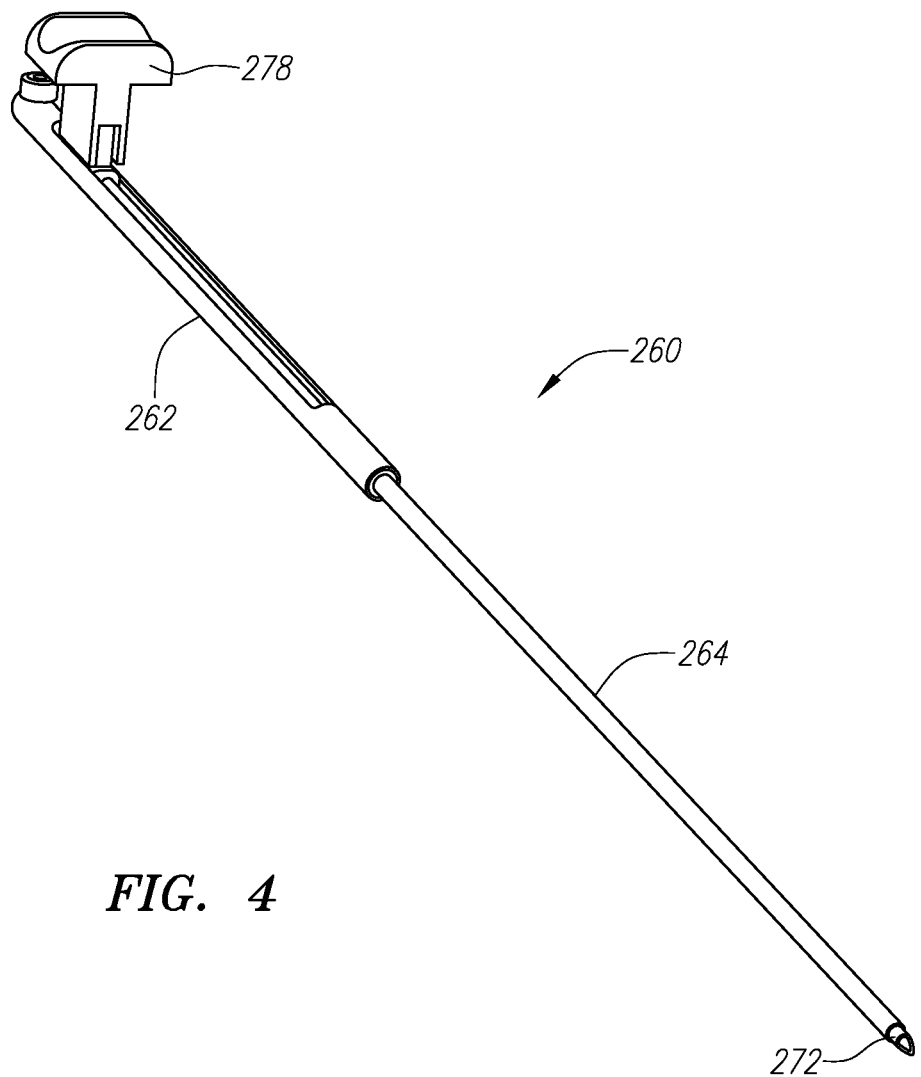
FIG. 4 is a perspective view of a second embodiment of an anchor deployment catheter.

The delivery device 208 shown in FIGS. 6-8 generally comprises a tissue manipulation assembly 210 and a needle deployment assembly 260. (Embodiments of the needle deployment assembly 260 are shown in FIGS. 3-5 and are described more fully below). The tissue manipulation assembly 210 includes a tubular body 212 that is configured to be substantially rigid for laparoscopic advancement via a trocar into the peritoneal cavity. The tubular body 212 is configured to be torqueable through various methods, e.g., utilizing a stainless steel or other substantially rigid tubular construction, such that when a handle 216 is manipulated and/or rotated by a practitioner from outside the patient's body, the longitudinal and/or torquing force is transmitted along the body 212 such that the distal end of the body 212 is advanced, withdrawn, or rotated in a corresponding manner.

A tissue manipulation end effector 214 is located at the distal end of the tubular body 212 and is generally used to contact and form tissue folds and/or to otherwise bring portions of tissue into apposition. Several embodiments of the distal end effector are shown in FIGS. 9A-E. In some embodiments, the tissue manipulation end effector 214 is connected to the distal end of the tubular body 212 via a pivotable coupling 218 formed on or attached to a manifold 219. A lower jaw member 220 extends distally from the pivotable coupling 218 and an upper jaw member 222, in this example, is pivotably coupled to the lower jaw member 220 via a jaw pivot 226. The location of the jaw pivot 226 may be positioned at various locations along the lower jaw 220 depending upon a number of factors, e.g., the desired size of the "bite" or opening for accepting tissue between the jaw members, the amount of closing force between the jaw members, etc. In other embodiments, the end effector 214 is connected to the distal end of the tubular body in a non-pivoting manner in which the lower jaw 220 is fixedly attached to the tubular body 212. One or both jaw members 220, 222 may optionally include a number of protrusions, projections, grasping teeth, textured surfaces, etc. on the surface or surfaces of the jaw members 220, 222 facing one another to facilitate the adherence of tissue between the jaw members 220, 222. In alternative embodiments, the surfaces of the jaw member 220, 222 are provided with a smooth, textured, or other atraumatic surface in order to decrease or eliminate the incidence of tissue injury.

Figure 9A:
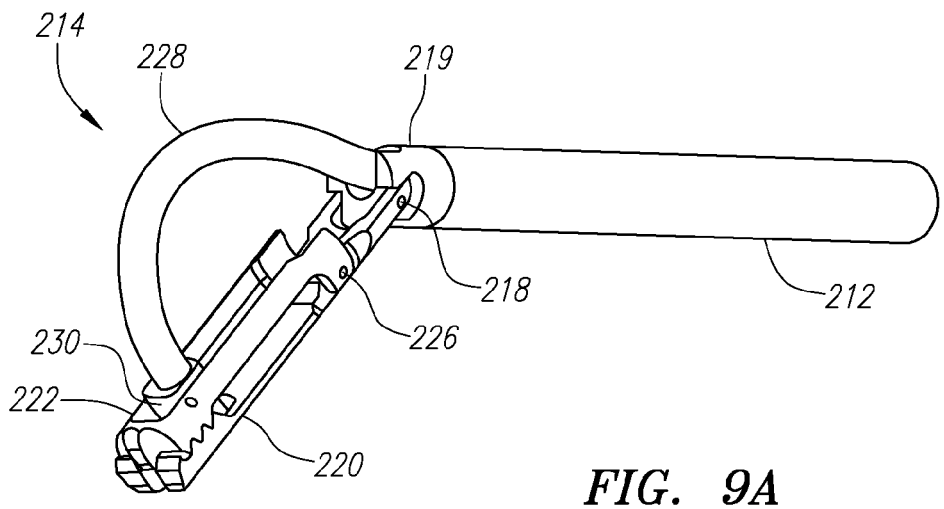
FIGS. 9A through 9E are perspective and side views of embodiments of end effectors of the laparoscopic tissue manipulation and anchor deployment device of FIG. 6.
Figure 9B:
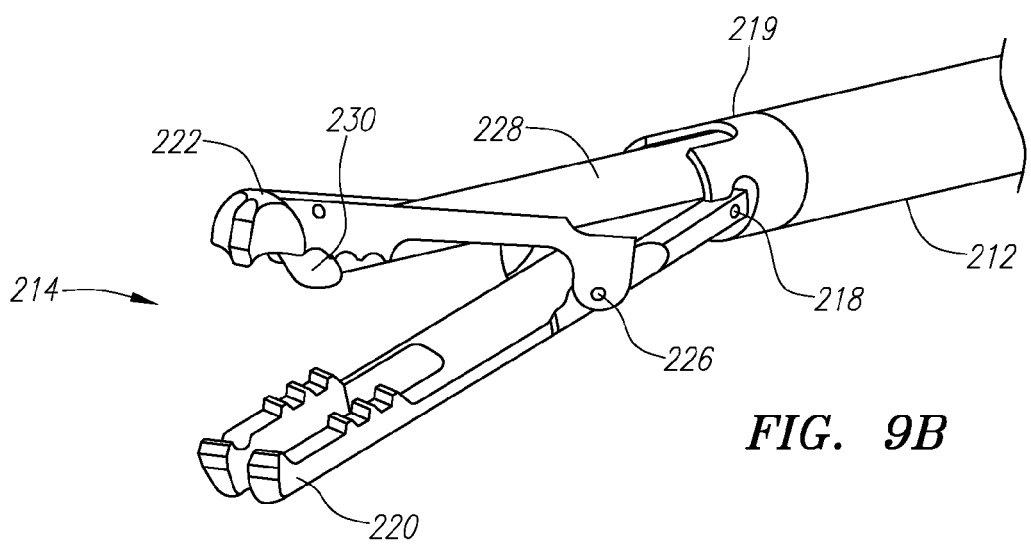
Figure 9C:
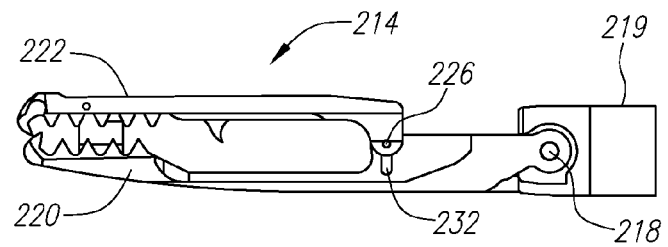
Figure 9D:
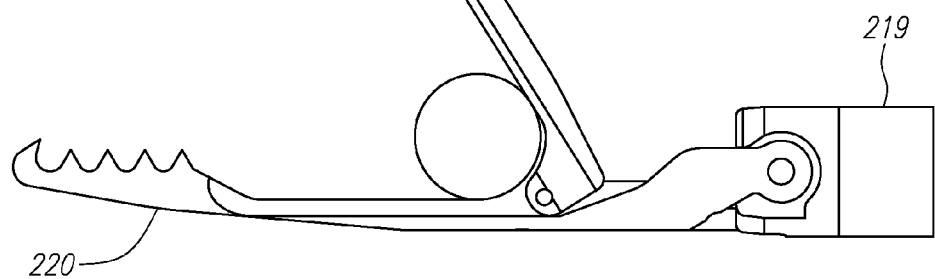
Figure 9E:
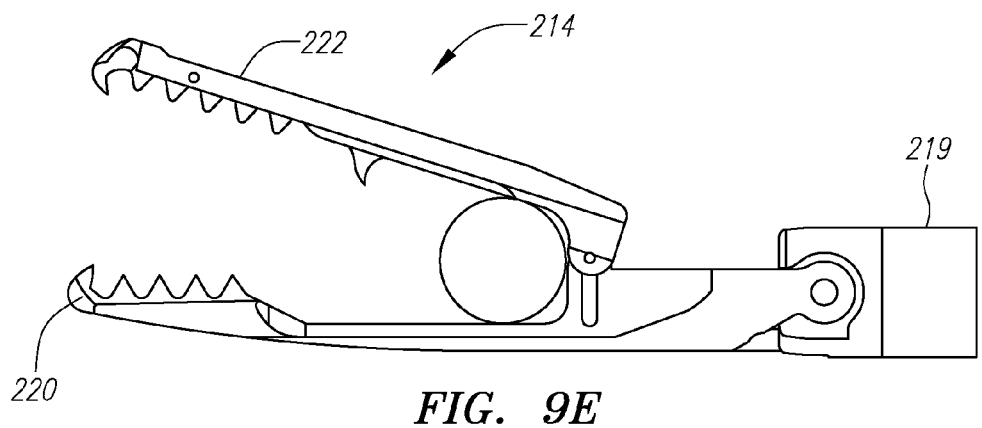

Turning to FIGS. 9C-E, three additional embodiments of the tissue manipulation end effector 214 are shown. For clarity, the tubular body 212 and launch tube 228 are not shown in the drawings. In the embodiment shown in FIG. 9D, the upper jaw 222 is pivotably coupled to the lower jaw 220 via a jaw pivot 226 that is fixedly attached to the lower jaw 220, as described above in relation to FIGS. 9A-B. In the embodiment shown in FIGS. 9C and 9E, a slotted jaw construction includes a jaw pivot 226 that is able to slide within an upright slot 232 formed in the frame of the lower jaw 220. In an alternative embodiment not shown, the jaw pivot 226 is fixed to the lower jaw 220 and slides within a slot 232 formed on the frame of the upper jaw 222. The capability of the jaw pivot 226 to slide within the upright slot 232 provides the end effector 214 with adjustable jaw geometries to better accommodate tissue folds (or other targets) having a wider range of sizes. For example, as shown by the illustrations in FIGS. 9D-E, the end effector 214 embodiment having the upright slot 232 (shown in FIG. 9E) is able to accommodate a comparably-sized target located at the vertex between the upper jaw 222 and lower jaw 220 without having to be opened as widely as is necessary with the end effector 214 embodiment that does not have the upright slot (shown in FIG. 9D). In addition, the vertex between the upper jaw 222 and lower jaw 220 in the embodiments having the upright slot 232 does not become a pinch point.

Those skilled in the art will recognize that the slotted jaw construction described above and shown in FIGS. 9C and 9E is adaptable for use in other laparoscopic instruments (or other instruments) having a pair of jaws oriented to grasp, trap, or engage tissue or other materials between the jaws. For example, the slotted jaw construction may be adapted for use with a laparoscopic stapling device in order to provide improved orientation between an upper staple cartridge and a lower anvil portion of the device. Other uses of the slotted jaw construction are also possible.

A launch tube 228 extends from the handle 216, through the tubular body 212, and distally from the end of the tubular body 212 where a distal end of the launch tube 228 is pivotally connected to the upper jaw member 222 at a launch tube pivot 230. A distal portion of the launch tube 228 may be pivoted into position within a channel or groove defined in the upper jaw member 222, to facilitate a low-profile configuration of the tissue manipulation end effector 214. When articulated, either via the launch tube 228 or other mechanism, the jaw members 220, 222 are urged into an open configuration to receive tissue in the opening between the jaw members 220, 222.

The launch tube 228 may be advanced from its proximal end at the handle 216 such that the portion of the launch tube 228 that extends distally from the tubular body 212 is forced to rotate at a hinge or pivot 230 and reconfigure itself such that the exposed portion forms a curved or arcuate shape that positions the launch tube opening perpendicularly relative to the upper jaw member 222. The launch tube 228, or at least the exposed portion of the launch tube 228, may be fabricated from a highly flexible material or it may be fabricated, e.g., from Nitinol tubing material which is adapted to flex, e.g., via circumferential slots, to permit bending.

Figure 10A:
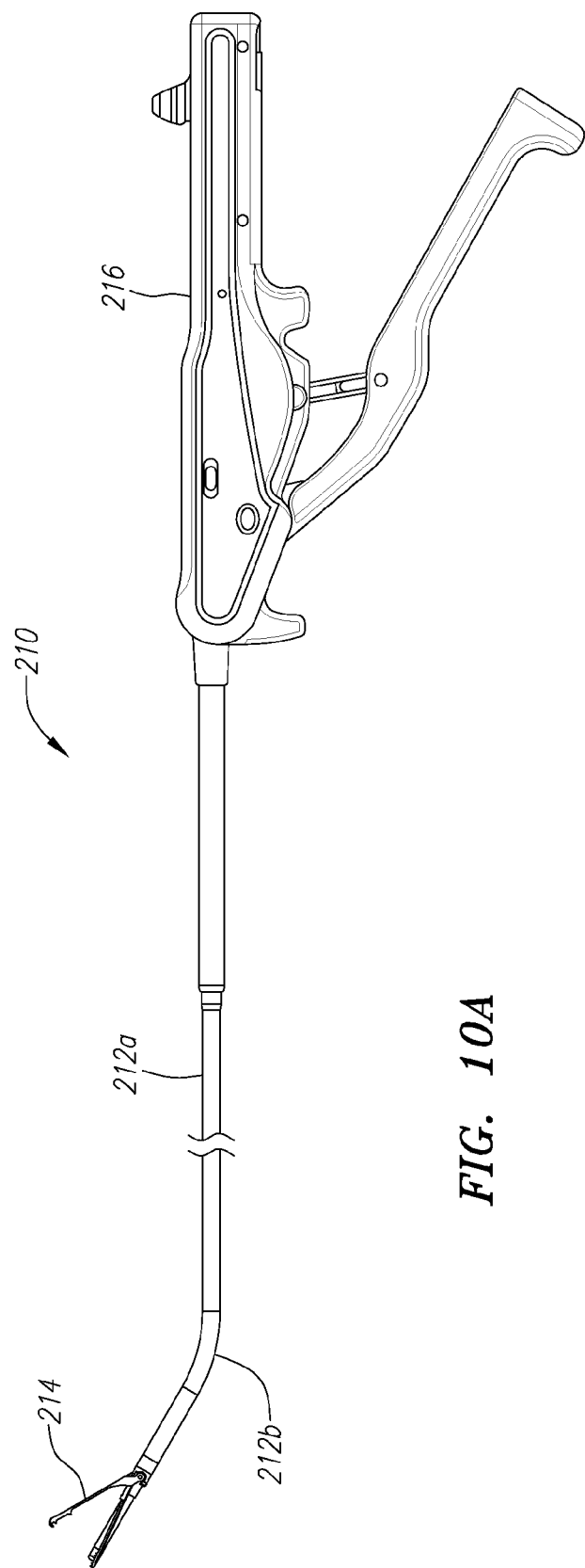
FIG. 10A is a side view of another embodiment of a laparoscopic tissue manipulation and anchor deployment device.
Figure 10B:
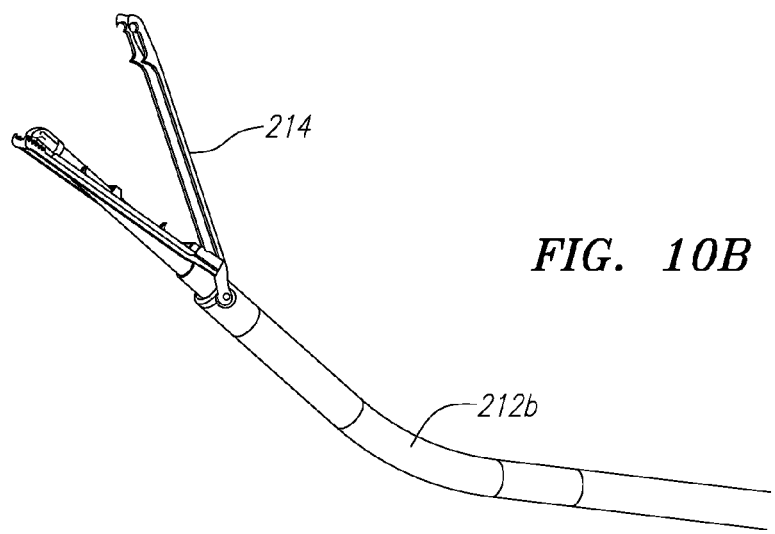
FIG. 10B is a side view of a distal region of the laparoscopic tissue manipulation and anchor deployment device shown in FIG. 10A.

In the embodiment of the tissue manipulation assembly 210 shown in FIG. 6, the tubular body 212 is substantially straight and is not articulatable. In other embodiments, such as those shown in FIGS. 10A-C, the tubular body 212 includes a substantially straight portion 212a extending from the handle 216 and a curved portion 212b on the distal region near the tissue manipulation end effector 214. The length, amount of curvature, and other aspects of the size, shape, and orientation of the curved portion 212b may depend upon the types of procedures to be performed. In some embodiments, the curved portion 212b creates an offset angle between the longitudinal axis of the proximal section 212a of the tubular body and the longitudinal axis of the distal region of the tubular body 212 and the end effector 214 of from about 5° to about 90°. In other embodiments, the offset angle is from about 20° to about 70°. In still other embodiments, the offset angle is from about 30° to about 60°. And in still other embodiments, the offset angle is about 45°.

In some embodiments, the curved portion 212b is formed from a material having a stiffness sufficient to maintain a shape during use by a surgeon or other user during a tissue manipulation procedure, but compliant enough to be manually straightened and inserted through a trocar. In this way, the user is able to manually straighten the instrument while inserting it through a straight, rigid trocar, after which the instrument would then spontaneously form into its shaped configuration. For example, in some embodiments, at least the curved portion 212b of the tubular body 212 is formed from a molded or heat set plastic or polymeric material having suitable hardness and/or flexibility. The curved portion 212b may include a curve in a selected plane relative to the plane of the end effector 214. For example, in an embodiment, the curved portion 212b of the distal region of the tubular body 212 is curved in the same plane as the plane of operation of the end effector 214. In other embodiments, the curved portion 212b of the distal region of the tubular body 212 is curved in a plane that is perpendicular to (or otherwise offset from) the plane of operation of the end effector 214.

In still other embodiments, the tubular body 212 includes a substantially straight portion 212a extending from the handle 216 and a steering section 212b on the distal region near the tissue manipulation end effector 214. Steering may be provided by one or more steering wires (push wires or pull wires), steering rods, or other suitable mechanisms that cause a steering section to be articulated in one or more planes relative to the plane of operation of the end effector 214 and/or relative to the region of the tubular body 212a located proximal to the steering section. The foregoing curved section or steering section 212b of the tubular body 212 may be provided in order to better provide the surgeon or other user with the capability of moving the distal end effector 214 to a preferred location relative to the target tissue of the patient.

Figure 10C:
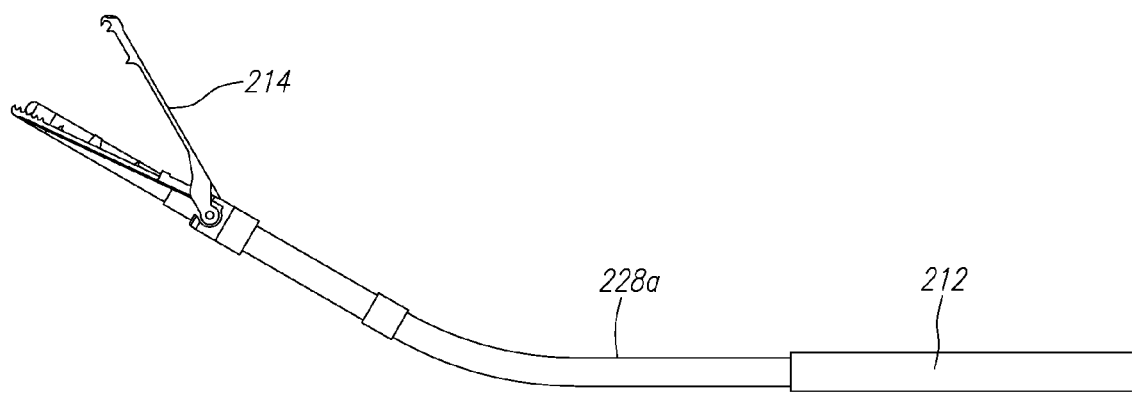
FIG. 10C is a side view of a distal region of the laparoscopic tissue manipulation and anchor deployment device shown in FIG. 10A shown with a portion of the tubular body removed for clarity.

Turning to FIG. 10C, some embodiments of the tissue manipulation assembly 210 include a flexible portion 228a of the launch/drive tube 228 that is located at the curved section or steering section 212b of the tubular body 212. The portions of the launch/drive tube 228 located proximally of the flexible portion 228a and housed within the rigid portion 212a of the tubular body 212 are typically formed of a rigid material, such as a stainless steel hypotube or other material. In order to translate through the curved section or steering section 212b of the tubular body 212, the flexible portion portion 228a of the launch tube is formed of a material having sufficient flexibility to be driven distally and withdrawn proximally around the curved portion 212b as the launch/drive tube 228 is translated through the tubular body 212 during actuation of the tissue manipulation end effector 214.

Turning next to FIGS. 11A-C, some embodiments of the tissue manipulation assembly 210 include a spring-loaded variable spacer 240 that is located in-line with the launch/drive tube 228 within the tubular body 212. The variable spacer 240 is positioned at a location between the handle 216 and the distal end effector 214, and preferably proximal of the curved section or steering section 212b of the tubular body 212. The variable spacer 240 includes a first collar or distal collar 241 that is attached to or formed integrally with a distal portion 228b the launch/drive tube to provide a distal shoulder for a compression spring 242 that is mounted coaxially over the launch/drive tube 228. A second collar 243 is attached to or formed integrally with the proximal end of the distal portion 228b of the launch/drive tube and defines a proximally-directed opening into the lumen defined by the launch/drive tube. A third collar or proximal collar 244 is attached to or formed integrally on the distal end of a proximal portion 228a of the launch/drive tube and is, in turn, attached to a piston sleeve 245 that has in inner diameter sufficient to allow the second collar 243 to slide therein, as shown in FIG. 11C. A fourth collar or sliding collar 246 is attached to a distal end of the piston sleeve 245 and is slidably retained on the external surface of the distal portion 228b of the launch/drive tube. The compression spring 242 is thereby retained between the distal collar 241 and the sliding collar 246 in the manner illustrated in FIG. 11C.

Accordingly, the distal portion 228b of the launch/drive tube is able to translate within the tubular body 212 relative to the proximal portion 228a of the launch tube/drive tube in a telescoping manner over a distance defined by the space between the distal collar 241 and the second collar 243. The compression spring 242 provides a force biasing the distal portion 228b and proximal portion 228a of the launch/drive tube apart. As described elsewhere herein, the distal end effector 214 is actuated by applying a compressive force on the launch/drive tube 228. The spring-loaded variable spacer 240 therefore provides a mechanism that prevents the launch/drive tube 228 from being over-compressed when, for example, the jaws 220, 222 of the end effector engage a large object (such as a large portion of tissue). Such over-compression could potentially cause damage to the launch tube 228 or other portions of the device.

Next, with reference to FIGS. 12A-G, some embodiments of the tissue manipulation assembly 210 include a distal end effector rotation mechanism 250 that is configured to rotate the distal end effector 214 relative to the tubular body 212. In the embodiment shown, the rotation mechanism 250 includes a housing or shield 251 that is attached to or formed integrally with the tubular body 212 and that includes one or more openings or access ports 252 that provide access to the user to an interior space defined by the shield 251. Located within the interior space defined by the shield 251 is a knob 253 that is attached to or formed integrally with the launch/drive tube 228, which is slidably disposed within the tubular body 212. Accordingly, by rotating the knob 253 around its longitudinal axis (which corresponds with the longitudinal axis of the launch/drive tube 228), the user is able to impart rotational movement to the launch/drive tube 228 relative to the tubular body 212. In addition, the knob 253 is able to advance (in the distal direction) or retract (in the proximal direction) within the interior space defined by the shield 251 by virtue of the fact that the knob 253 is attached to or formed integrally with the launch/drive tube 228. Accordingly, as the user actuates the handle 216 to cause the launch/drive tube 228 to advance and retract relative to the tubular body 212, the knob 253 is advanced and retracted within the interior space provided by the shield 251. (Compare, e.g., the proximal position of the knob 253 in FIG. 12B to the distal position of the knob 253 in FIG. 12C).

Figure 12A:
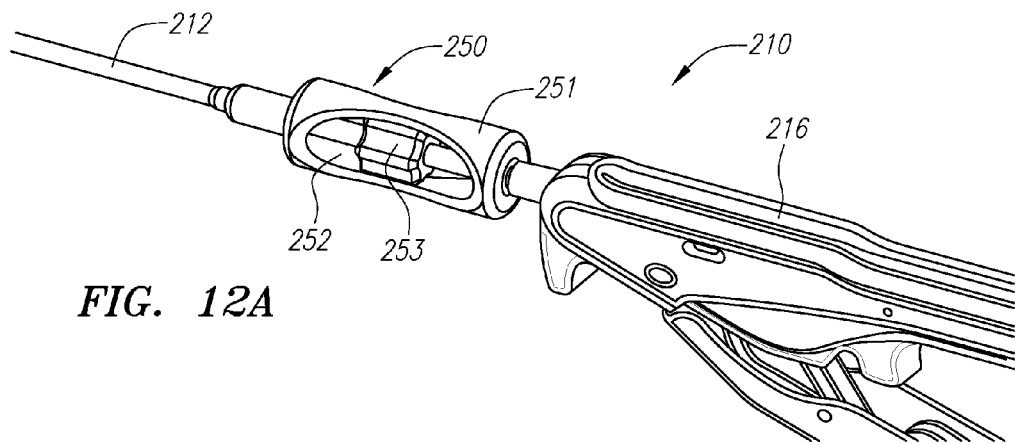
FIGS. 12A-C are perspective and two side views, respectively, of an embodiment of a laparoscopic tissue manipulation and anchor deployment device having a distal end effector rotation mechanism.
Figure 12B:
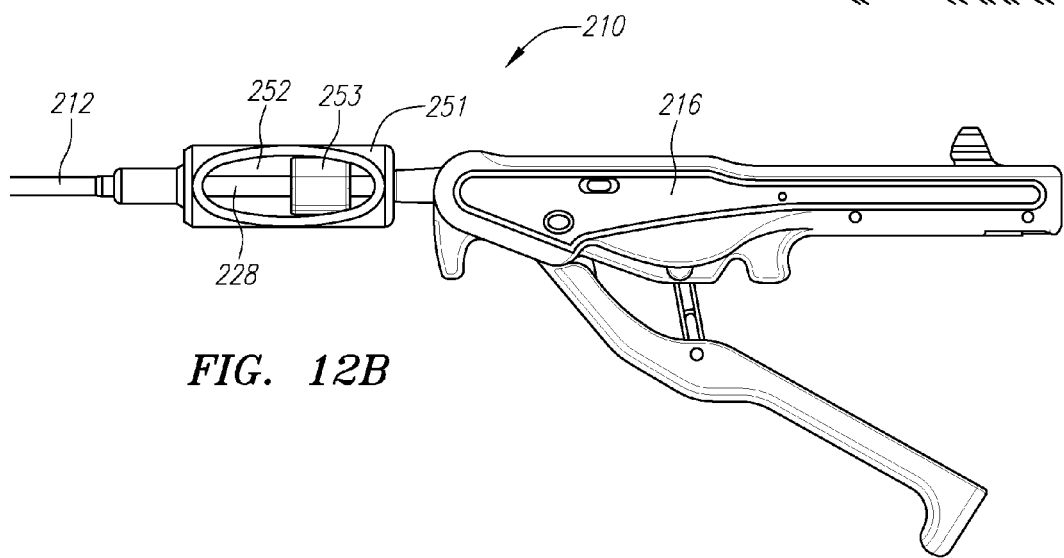
Figure 12C:
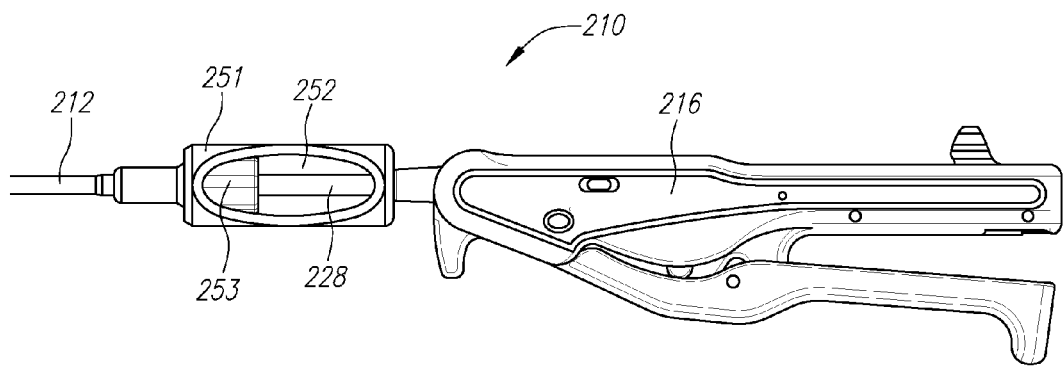

In the embodiment shown in FIGS. 12A-C, the distal end effector 214 (which is coupled to the launch tube 228) is rotatably supported on the distal end of the tubular body 212. Accordingly, rotating the launch/drive tube 228 relative to the tubular body 212—via rotating the knob 253 relative to the shield 251—causes the distal end effector 214 to rotate relative to the tubular body 212. An embodiment of a suitable rotatable connection between the distal end effector 214 and the tubular body 212 is shown in FIGS. 12D-G. The rotatable connection embodiment shown includes a rotatable sleeve 254 that is inserted into the proximal end of the manifold 219, as shown in FIGS. 12E-F. The rotatable sleeve 254 includes a distal flange 254a that has an outer diameter that is slightly smaller than the inner diameter of the manifold 219, thereby allowing the rotatable sleeve 254 to rotate freely relative to the manifold 219. A collar 255 is then placed over the rotatable sleeve 254 and is attached to (such as by welding or otherwise bonding) the inner surface of the manifold 219, creating an annular space within the manifold 219 that rotatably traps the distal flange 254a of the rotatable sleeve 254. (See FIG. 12G). The tubular body 212 is then attached to the outer surface 254b of the rotatable sleeve, thereby providing the rotatable connection shown in FIG. 12D. Those skilled in the art will recognize that other rotatable connection mechanisms may be suitable for providing the rotatable connection between the distal end effector 214 and the tubular body 212.

Figure 13:
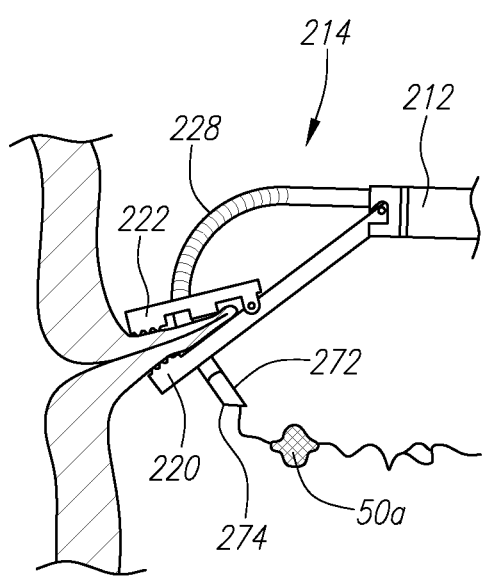
FIG. 13 is a side view of the distal end effector of an embodiment of the laparoscopic tissue manipulation and anchor deployment device of FIG. 6 deploying a tissue anchor assembly through a region of tissue.

Turning back to FIGS. 3-5, once the tissue has been engaged between the jaw members 220, 222 of the tissue manipulation assembly 210, a needle deployment assembly 260 is urged through the handle 216, though the tubular body 212, and out through the launch tube 228. Embodiments of the needle deployment assembly are shown in FIGS. 3-5, and are described in substantial detail in U.S. patent application Ser. Nos. 10/955,245, 11/070,863, and 12/486,578, which are hereby incorporated by reference in their entireties (including all references cited therein) as if fully set forth herein. The needle deployment assembly 260 may pass through the lower jaw member 220 via a needle assembly opening (not shown in the drawings) defined in the lower jaw member 220 to pierce through the grasped tissue. Once the needle deployment assembly has been passed through the engaged tissue, one or more tissue anchors 50a of a tissue anchor assembly 100 (see FIG. 13) are deployed for securing the tissue, as described in further detail herein and in U.S. patent application Ser. No. 10/955,245, which has been incorporated by reference above.

Referring to FIGS. 3-5, each shows additional details relating to embodiments of a needle deployment assembly 260. As mentioned above, a needle deployment assembly 260 may be deployed through the tissue manipulation assembly 210 by introducing the needle deployment assembly 260 into the handle 216 and through the tubular body 212 such that the needle deployment assembly 260 is advanced from the launch tube 228 and into or through grasped tissue. Once the needle deployment assembly 260 has been advanced through the tissue, the anchor assembly 100 may be deployed or ejected. The anchor assembly 100 is normally positioned within the distal portion of a tubular sheath 264 that extends from a needle assembly control or housing 262. Once the anchor assembly 100 has been fully deployed from the sheath 264, the spent needle deployment assembly 260 may be removed from the tissue manipulation assembly 210 and another needle deployment assembly may be introduced without having to remove the tissue manipulation assembly 210 from the patient. The length of the sheath 264 is such that it may be passed entirely through the length of the tubular body 212 to enable the deployment of the needle deployment assembly 260 into and/or through the tissue.

The elongate sheath or catheter 264 extends removably from the needle assembly control or housing 262. The sheath or catheter 264 and the housing 262 may be interconnected via an interlock 270 which may be adapted to allow for the securement as well as the rapid release of the sheath 264 from the housing 262 through any number of fastening methods, e.g., threaded connection, press-fit, releasable pin, etc. The needle body 272, which may be configured into any one of the variations described above, extends from the distal end of the sheath 264 while maintaining communication between the lumen of the sheath 264 and the needle opening 274.

An elongate pusher 276 comprises a flexible wire, coil, or hypotube that is translationally disposed within the sheath 264 and movably connected within the housing 262. A proximally-located actuation member 278 is rotatably or otherwise connected to the housing 262 to selectively actuate the translational movement of the elongate pusher 276 relative to the sheath 264 for deploying the anchors from the needle opening 274. The tissue anchor assembly 100 is positioned distally of the elongate pusher 276 within the sheath 264 for deployment from the sheath 264. Needle assembly guides 280 protrude from the housing 262 for guidance through the locking mechanism described above.

Turning to FIGS. 14A-D and 15A-F, in some embodiments, the needle deployment assembly 260 provided in the tissue anchor delivery device 208 with an anchor retention mechanism that facilitates deployment of a single anchor of a tissue anchor assembly 100 without inadvertently deploying both anchors of the assembly. FIGS. 14A-D and 15A-F illustrate the distal portion of a sheath 264 and needle body 272 of a needle deployment assembly 260. The remaining portions of the delivery device 208 have been omitted only for clarity.

Figure 14A:
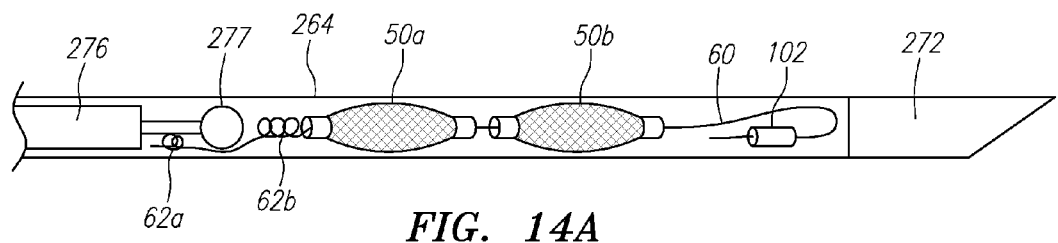
FIGS. 14A-D are side cross-sectional view of four embodiments of an anchor retention mechanism.

In the embodiment shown in FIG. 14A, the elongate pusher 276 is provided with an extension arm 277 having an enlarged portion at its distal end. The enlarged portion of the extension arm 277 traps a first knot 62a formed at a proximal end of the suture of the tissue anchor assembly 100 within the interior space of the sheath 264. A second knot 62b formed distally of the first knot 62a is attached (e.g., with glue or other adhesive) to the distal anchor 50a, thereby providing the pusher 276—to which the extension arm 277 is attached—with the capability of positively controlling the position of the distal anchor 50a within the sheath 264. Accordingly, as the pusher 276 is advanced distally within the sheath 264, the distal anchor 50a (and the components that are within the sheath 264 distal of the distal anchor) will be advanced distally. As the pusher 276 is retracted proximally within the sheath 264, the distal anchor 50a will be retracted proximally. This capability reduces the possibility that the distal anchor 50a will be deployed inadvertently.

Figure 14B:
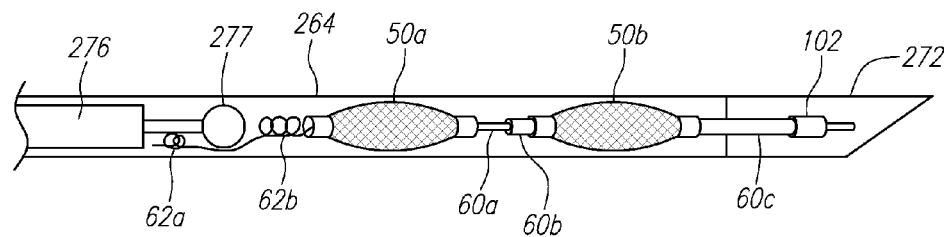

The embodiment shown in FIG. 14B is similar to the one shown in FIG. 14A, except rather than having the distal anchor 50a being adhered to the second knot 62b, the distal anchor 50a is prevented from moving distally relative to the suture 60 by the inclusion of a step up in thickness of the suture relative to the diameter of the passageway through the distal anchor 50a. For example, the suture has a first thickness at region 60a that is small enough that the distal anchor 50a is able to slide freely back and and forth along the suture 60a. However, at region 60b, the suture has a thickness that is larger, such that the distal anchor 50b is not able to traverse the transition from region 60a to region 60b. In this way, the distal anchor 50a is thereby trapped within a pre-determined region of travel by the elongate pusher 276, thereby reducing the possibility that the distal anchor 50a will be deployed inadvertently.

Figure 14C:
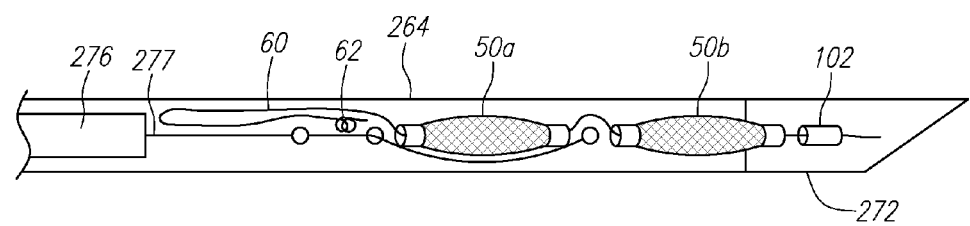
Figure 14D:
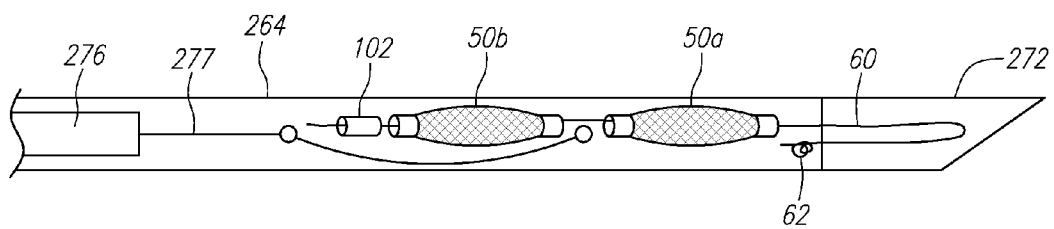

In the embodiments shown in FIGS. 14C and 14D, the extension arm 277 includes a region that physically traps the entire distal anchor 50a, thereby directly controlling the location of the distal anchor with the pusher 276.

Figure 15A:
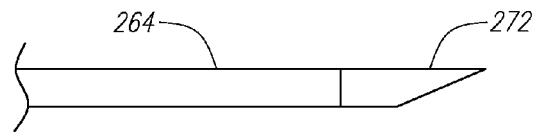
FIGS. 15A-F are illustrations of the progression of an anchor deployment method using an anchor retention mechanism.
Figure 15B:
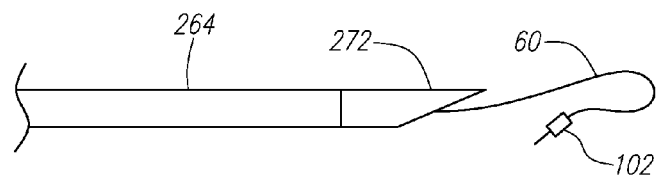
Figure 15C:
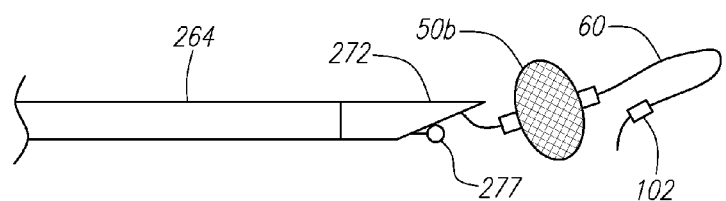
Figure 15D:
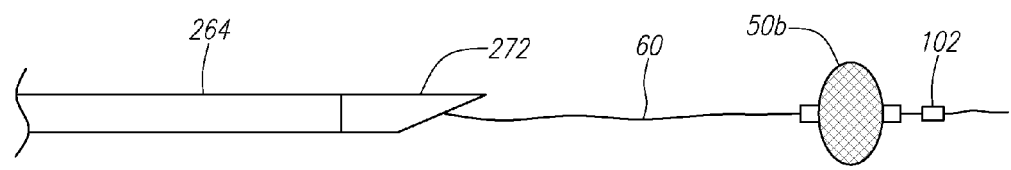
Figure 15E:
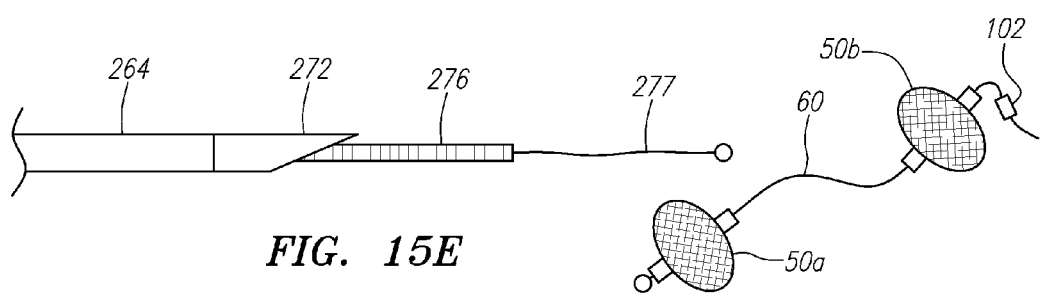
Figure 15F:
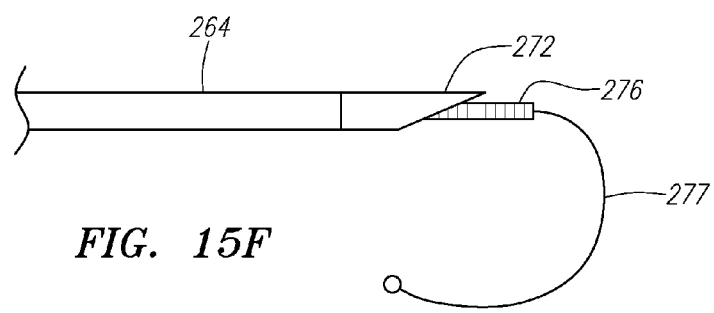

Turning to FIGS. 15A-F, the manner of operation of the retention mechanisms described above is shown. A needle 272 and sheath 264 of a needle deployment assembly 260 are deployed from a tissue anchor deployment device 208. As the pusher 276 is advanced, the cinch 102 and suture 60 are expelled from the distal end of the needle body 272, as shown in FIG. 15B. Further advancement of the pusher 276 causes the proximal anchor 50b to be expelled. (See FIG. 15C). In FIG. 15C, the enlarged distal end of the extension arm 277 is seen extending from the distal opening of the needle body 272, but the distal anchor 50a remains held within the sheath 264. As the deployment device 208 is retracted, such as when the device is moved to the location of a second tissue fold, the suture 60 is paid out, as shown in FIG. 15D. Finally, the pusher 276 is fully extended outside of the sheath 264 and needle body 272, thereby releasing the distal anchor 50a. (See FIG. 15E). In an alternative embodiment, the extension arm 277 is provided with a shape memory curve, (see FIG. 15F), to prevent inadvertent engagement or interference with the target tissue.

After the tissue anchor assembly 100 is deployed using any of the deployment devices and embodiments described herein, the locking mechanism 102 of the tissue anchor assembly 100 may be advanced uni-directionally over the suture 60 to thereby secure a region of tissue between the pair of tissue anchors 50a, 50b. In some embodiments, the locking mechanism 102 is advanced using a grasper, knot pusher, or other suitable instrument. For example, in some embodiments, a cinch tool is adapted to grasp the suture 60 and to apply a force that advances the locking mechanism 102 over the suture 60. Several cinch tool embodiments are described in U.S. patent application Ser. No. 10/954, 665, filed Sep. 29, 2004, and in U.S. Pat. No. 7,390,329, each of which is incorporated by reference in its entirety.

Figure 16:
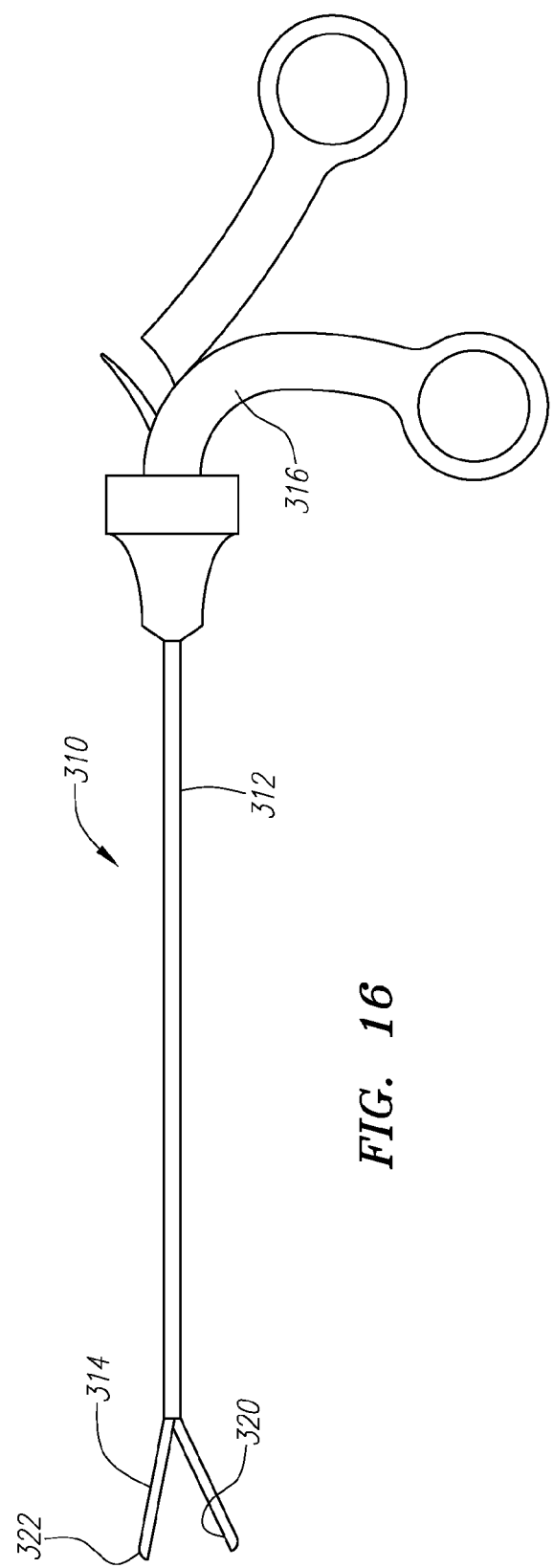
FIG. 16 is a side view of a laparoscopic instrument.
Figure 17A:
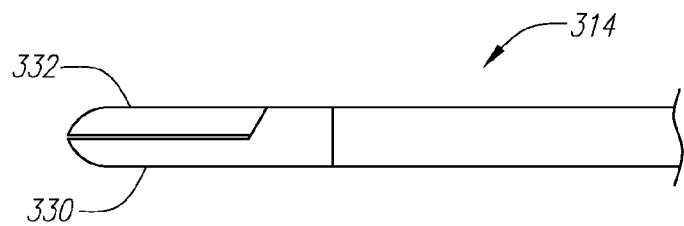
FIGS. 17A through 17D are side views of alternative end effectors for the laparoscopic instrument of FIG. 16.
Figure 17B:
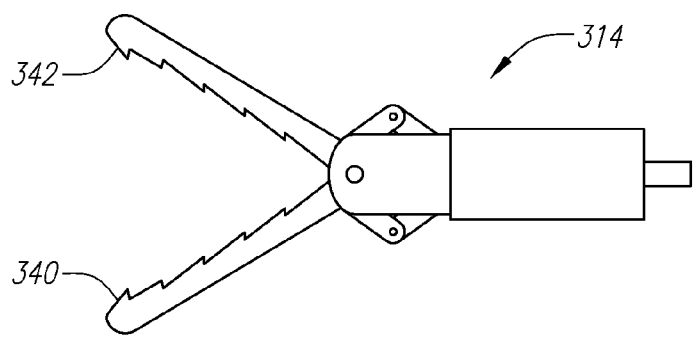
Figure 17C:
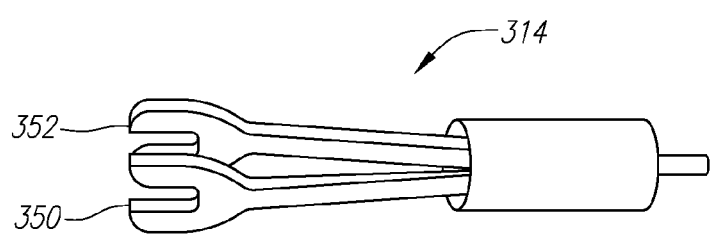
Figure 17D:
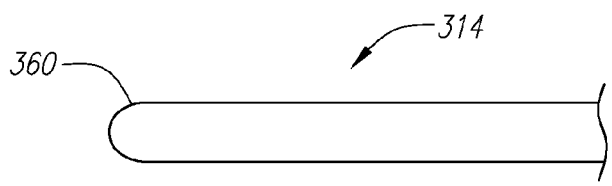

The laparoscopic tissue anchor delivery device 208 is typically used in conjunction with one or more additional laparoscopic instruments to perform the tissue reconfiguration procedures described herein. Several conventional laparoscopic instruments are known to those having ordinary skill in the art, and the details of those instruments are beyond the scope of the present description. FIG. 16 is an exemplary illustration of a laparoscopic instrument 310 having a shaft 312, an end effector 314, and a handle 316. In the embodiment shown, the instrument includes a substantially rigid shaft 312 and an end effector 314 in the form of a grasper having a pair of grasping jaws 320, 322. In FIGS. 17A-D, several alternative end effector embodiments are shown, including an alternative pair of grasping jaws 330, 332 shown in FIG. 17A, a pair of alligator grasper jaws 340, 342 shown in FIG. 17B, a pair of tong-style grasping members 350, 352 shown in FIG. 17C, and a blunt obturator 360 shown in FIG. 17D. Other optional laparoscopic instruments are suitable for use, including Babcock-style graspers, Maryland-style graspers, and other devices known to those skilled in the art.

Figure 18:
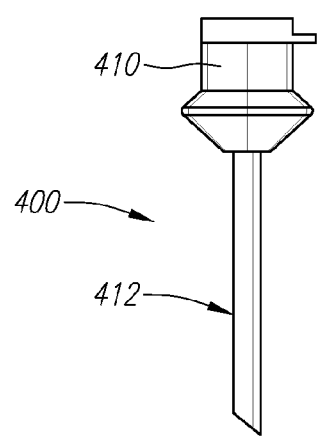
FIG. 18 is a side view of a trocar.

FIG. 18 illustrates a conventional trocar 400, including a cannula head portion 410 and a cannula tube portion 412. In some embodiments, the cannula tube portion 412 is flexible to facilitate additional ranges of motion for the laparoscopic instruments used to perform the described procedures. The procedures described herein make use of known trocars 400 and the specific type of trocar 400 to be used by a surgeon may be left to the personal preference of the surgeon.

Laparoscopic Hernia Repair

Novel procedures for repairing a patient's incisional or other type of hernia will be described. The procedures overcome many of the disadvantages associated with prior art methods by providing a hernia repair that is easy to perform, has a low recurrence rate, has a minimal peri-operative morbidity, and is cost effective. The methods are performed laparoscopically and include deployment of one or more tissue anchor assemblies or other tissue fasteners that facilitate approximation of the opposed edges of a hernia defect. For clarity, the disclosure below will include a description of methods for repairing an incisional hernia. It should be understood that the described methods are also applicable to the repair of other types of hernia, unless otherwise stated.

Figure 19:
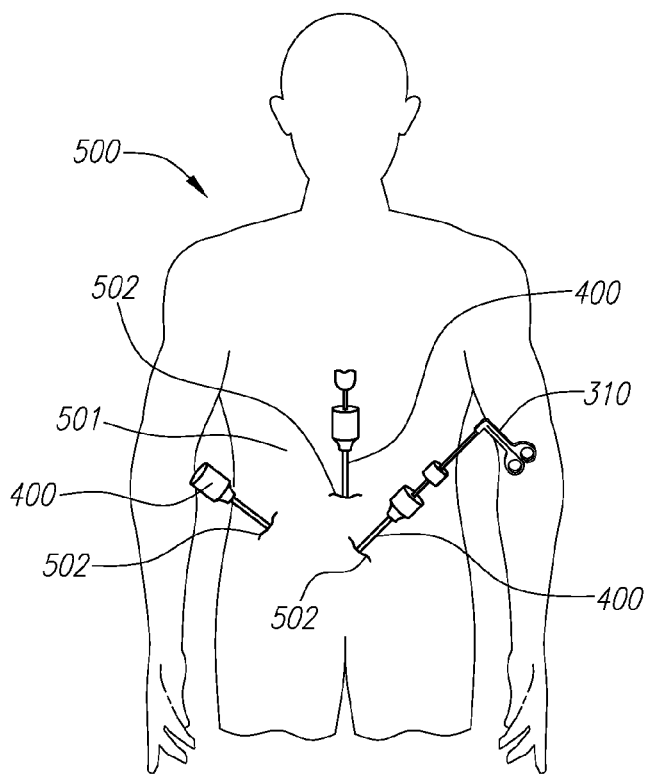
FIG. 19 is a top view illustrating a laparoscopic procedure being performed on a patient.

Turning to FIG. 19, the procedure includes placing the patient 500 in a supine position, which is typical in abdominal surgery. In order to determine the location of the hernia opening inside the abdomen 501, a conventional cut-down method is used to enter the abdominal cavity at a site away from the hernia. The initial incision 502 of the cut-down method is no more than 10-12 mm. This initial incision allows for the placement of a blunt trocar 400 through the incision and into the peritoneal cavity. With the trocar in place, the abdomen is insufflated with 15 mm Hg pressure of carbon dioxide gas. A laparoscope is then introduced through the trocar 400 to inspect the interior of the abdomen and the abdominal wall. If the inspection reveals any evidence of adhesions near the hernia site which are required to be lysed or dissolved, or of incarceration or confinement of tissues, which needs to be reduced, additional 5-10 mm trocars 400 and laparoscopic working instruments 310 are introduced into the abdomen 501 under direct vision for this purpose.

Figure 20:
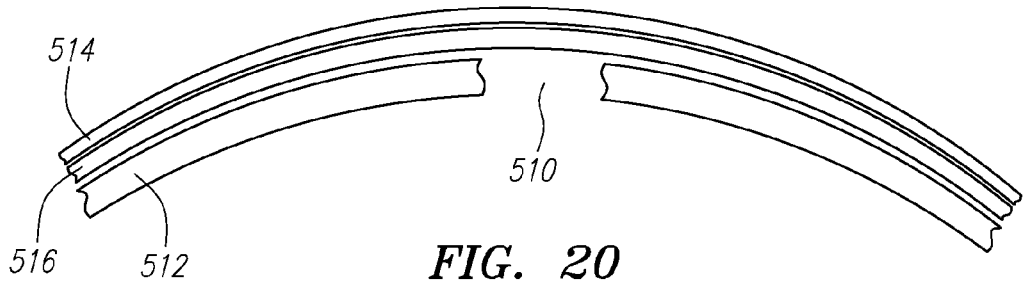
FIG. 20 is a cross-sectional view showing a hernia defect in the fascia tissue of a patient.

As shown in FIG. 20, a hernia is a hole 510 in the fascia 512 of the abdominal wall and allows the inner lining of the abdominal wall to protrude or bulge. The bulge forms a balloon-like sac (hernia sac) beneath the skin 514 and fat layers 516 beneath the skin. Intra-abdominal contents such as fat or loops of intestine can also protrude through the defect 510 in the fascia 512 and into the hernia sac. Loops of intestine or fat can become trapped (incarcerated) or twisted (strangulated) in the hernia sac and block the flow of food in the intestinal tract or compromise its blood supply. Although this is very rare, strangulation may lead to a potentially life threatening and serious problem requiring emergency surgery. Hernias occur in the abdominal wall where the fascia 512 is compromised, most commonly in the groin (inguinal hernias), and areas of previous surgical incisions (ventral hernias). Hernias tend to grow larger over time and can become symptomatic.

Figure 21:
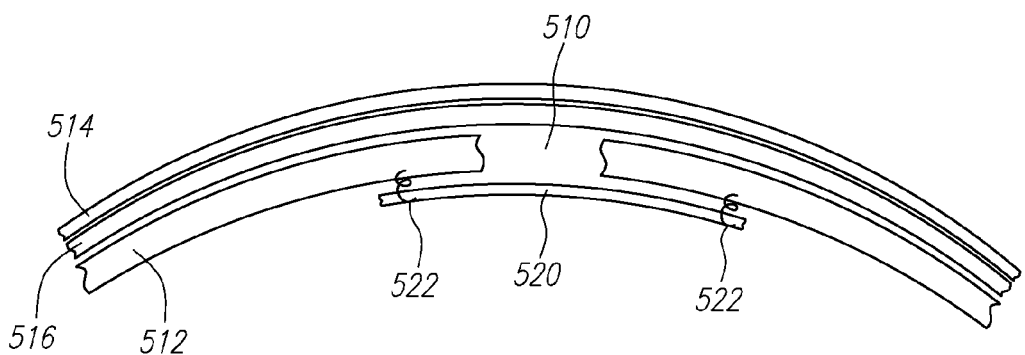
FIG. 21 is a cross-sectional view showing the hernia defect of FIG. 20 after deployment of a surgical mesh.

In a conventional laparoscopic hernia repair, shown in FIG. 21, a surgical mesh 520 is applied over a weakened area or defect 510 in the abdominal wall. The mesh 520 is sewn to the area or attached with fasteners such as tacks 522, bridging the hole 510 or weakened area beneath it. As the area heals, the mesh 520 becomes firmly integrated into the inner abdominal wall membrane (peritoneum) that protects the organs of the abdomen. One disadvantage of the conventional procedure is that the separated portions of the fascia 512 are not brought together, with the result that the defect 510 remains in place after the procedure is completed. As a result, the mesh 520, along with the intra-abdominal fat, loops of intestine, and other contents are still able to protrude through the defect 510.

In several embodiments of the procedures described herein, the portions of the fascia 512 that are separated by the occurrence of the hernia are brought together by deploying one or more tissue anchor assemblies 100 or other types of tissue fasteners across the defect 510. The first and second anchors 50a, 50b of the tissue anchor assemblies 100 are then approximated and secured, thereby approximating the separated edges of the fascia 512 and reducing or eliminating the hernia defect 510. In other embodiments, the separated edges of the fascia 512 are approximated prior to deploying the tissue anchor assemblies 100 or other types of tissue fasteners. A surgical mesh 520 is then attached to the fascia 512 over the approximated defect 510. In other embodiments, the tissue anchor assemblies 100 or other types of fasteners are sufficient to repair the hernia defect without the use of a surgical mesh 520, and the mesh 520 is therefore not attached to the fascia 512. Exemplary embodiments of the methods are described more fully below, with reference to FIGS. 22 through 27A-D.

Figure 22:
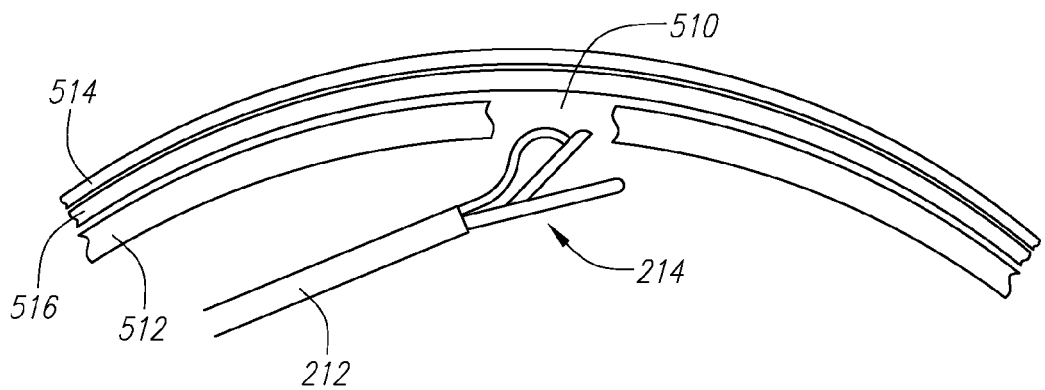
FIGS. 22-24 are cross-sectional views showing the progression of a portion of a laparoscopic hernia repair procedure.

As shown in FIG. 22, a tissue manipulation end effector 214 of a tissue anchor deployment device is inserted through a trocar and into the peritoneal space, and is brought into the vicinity of the hernia defect 510 and, more particularly, into the vicinity of the edges of the fascia 512 surrounding the hernia defect 510. As described more fully above, the exemplary tissue anchor deployment device described herein includes a needle deployment assembly 260, the distal end of which is translatably located within the launch tube 228 portion of the tissue anchor deployment device.

The jaws 220, 222 of the tissue manipulation end effector 214 are used to grasp a first one of the edges of the fascia 512a surrounding the hernia defect 510. In some embodiments, the first edge of the fascia 512a and/or other tissue associated with the hernia defect is separated from adjacent or surrounding tissue using a component separation technique known to those skilled in the art. In the embodiments in which a component separation technique is included, the separation of the fascia 512a from other associated tissue and/or tissue layers facilitates manipulation of the tissue by reducing the amount of tension required to approximate the opposed edges of tissue at the hernia defect. This result, in turn, allows the surgeon or other user to manipulate and/or approximate the tissue more easily, such that the procedure is simplified and the defect is repaired more readily. Moreover, in some embodiments, another laparoscopic instrument 310, such as a laparoscopic grasper, is used to facilitate grasping of the first fascia edge 512a by the end effector 214.

Figure 23:
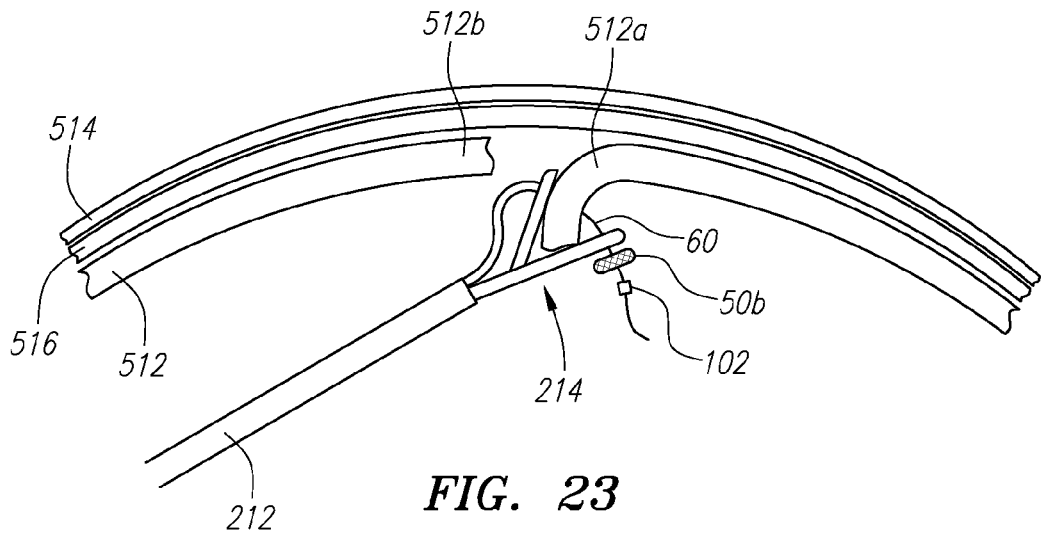
Figure 24:
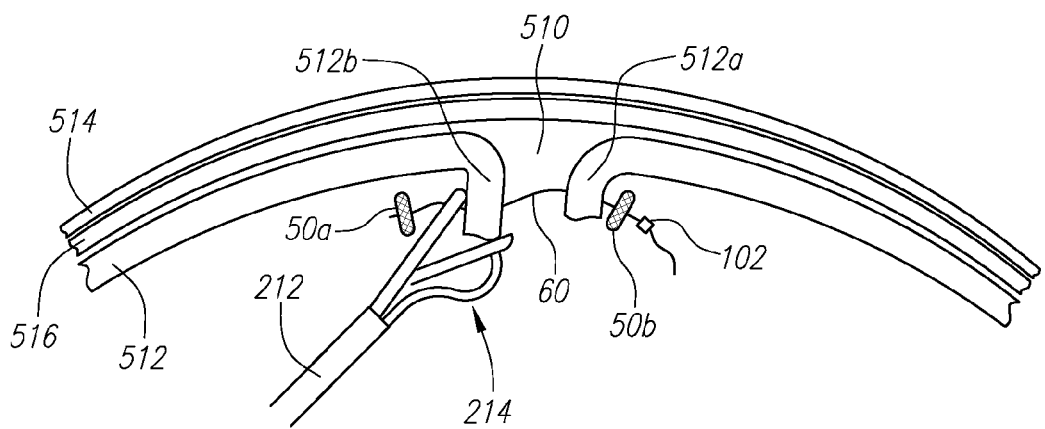

After the first fascia edge 512a is engaged, the second anchor 50b (or other fastener) and cinch 102 (or other locking mechanism) are then deployed from the device via the needle deployment assembly 260 through the grasped region of the fascia 512a, as shown in FIG. 23. In the embodiment shown, the first fascia edge 512a is grasped by the jaws 220, 222 of the end effector 214 such that the second anchor 50b and cinch 102 are deployed on the peritoneal side of the first fascia edge 512a. The first fascia edge 512 is then released, and the end effector 214 is repositioned to grasp a second of the edges of the fascia 512b located substantially opposite to the first fascia edge 512a across the hernia defect 510. The suture 60 of the tissue anchor assembly 100 extends out of the needle deployment assembly 260 located within the launch tube 228 of the device, through the first fascia edge 512, and through the second tissue anchor 50b. As shown in FIG. 24, the needle deployment assembly 260 is then advanced through the second fascia edge 512b, where the first tissue anchor 50a is deployed. In the embodiment shown, the second fascia edge 512b is grasped by the jaws 220, 222 of the end effector 214 such that the first anchor 50a is also deployed on the peritoneal side of the second fascia edge 512b.

Figure 25A:
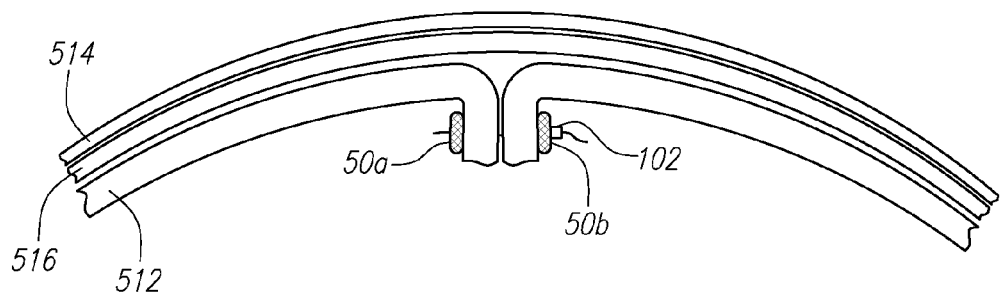
FIGS. 25A-B are cross-sectional views showing a tissue anchor assembly deployed through opposed edges of fascia tissue in a side-by-side orientation and an overlapping orientation, respectively.
Figure 25B:
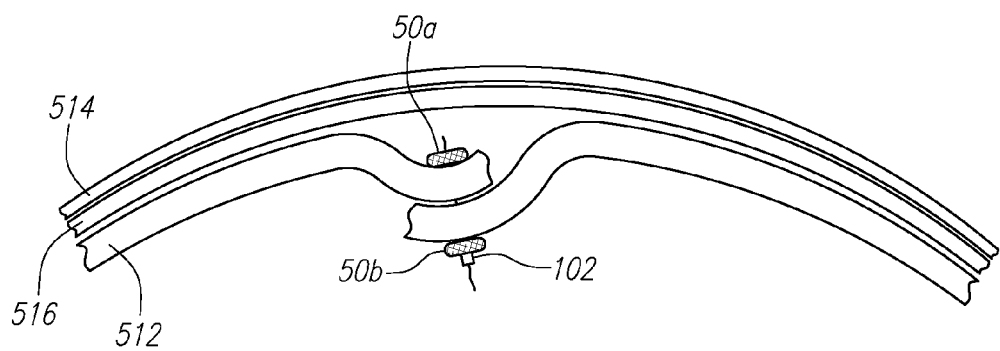

In several embodiments, a plurality of additional tissue anchor assemblies 100 are deployed adjacent to one another along the length of the hernia defect 510. Turning to FIG. 25A, after the first and second tissue anchors 50a, 50b of each of the plurality of tissue anchor assemblies 100 have been deployed through the first fascia edge 512a and second fascia edge 512b, the uni-directional cinch 102 of each tissue anchor assembly 100 is advanced over the suture 60 to thereby cause the tissue anchors 50a, 50b to be approximated and to cause the first fascia edge 512a to be brought into proximity to the second fascia edge 512b in a side-by-side orientation. In an alternative embodiment, shown in FIG. 25B, the second tissue anchors 50b are deployed through the second fascia edge 512b in the opposite direction to that shown in FIG. 21, i.e., such that the second tissue anchor 50b is located on the side of the fascia opposite to the peritoneal cavity. The uni-directional cinch 102 of each tissue anchor assembly 100 is advanced over the suture 60 to thereby cause the tissue anchors 50a, 50b to be approximated and to cause the first fascia edge 512a to be brought into proximity to the second fascia edge 512b in an overlapping orientation.

In some embodiments, the plurality of tissue anchor assemblies 100 provide sufficient holding strength to maintain the first and second fascia edges 512a, 512b in proximity to one another permanently, thereby repairing the hernia defect 510. In other embodiments, the plurality of tissue anchor assemblies 100 provide sufficient holding strength to maintain the first and second fascia edges 512a, 512b in proximity to one another for a time sufficient to promote healing between the secured fascia edges, thereby repairing the hernia defect 510. In still other embodiments, the first and second fascia edges 512a, 512b are oversewn with a suture or other suitable member in the manner described below in relation to FIG. 27D in order to further secure the approximated fascia edges in proximity to one another.

Figure 26:
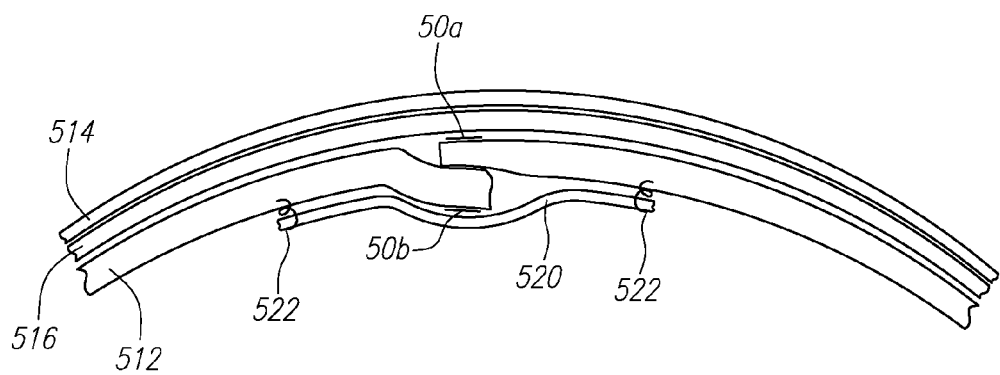
FIG. 26 is a cross-sectional view of a repaired incisional hernia.

Turning to FIG. 26, after approximating the first fascia edge 512a and second fascia edge 512b, an optional surgical mesh 520 is applied to the abdominal tissue such that the mesh 520 fully or substantially covers the reduced or eliminated defect 510. Advantageously, a smaller surgical mesh 520 will be needed in the typical procedure after the fascia edges 512a, 512b in the vicinity of the hernia defect 510 have been approximated than would otherwise be needed without the tissue approximation. As a result, the surgical mesh 520 may be more easily deployed, heals better and more readily, and is less likely to pucker or to become displaced after deployment. As discussed above, some embodiments of the repair methods described herein do not include application of the surgical mesh. The surgical mesh patch 520 is well known in the art. It is constructed of a mesh material which allows bodily tissue growth into the mesh to further stabilize the position of the mesh patch 520 at some point subsequent to surgery. The mesh patch 520 is known to be constructed of many different materials, including but not limited to, Gore-Tex® fabric, polytetraflouroethylene, or polypropylene. The procedures described herein make use of known mesh patches 520 and the specific type, size, and other properties of the mesh patch 520 to be used by a surgeon may be left to the personal preference of the surgeon.

The surgical mesh 520 is secured to the internal surface of the fascia 512 using suture or other fasteners, such as surgical tacks 522, in a manner known to those skilled in the art. In the embodiment shown in FIG. 26, the first and second fascia edges 512a, 512b are approximated by a plurality of tissue anchor assemblies 100 in an overlapping orientation, as described above in relation to FIG. 25B. The overlapping orientation provides a "ridge" along the reduced or eliminated defect 510 that has a lower profile than the ridge provided by the side-by-side orientation described above in relation to FIG. 25A. The lower profile size of the ridge allows the mesh 520 to more readily engage the underlying fascia 512, thereby promoting faster and more complete ingrowth of tissue throughout the extent of the surgical mesh 520.

Figure 27A:
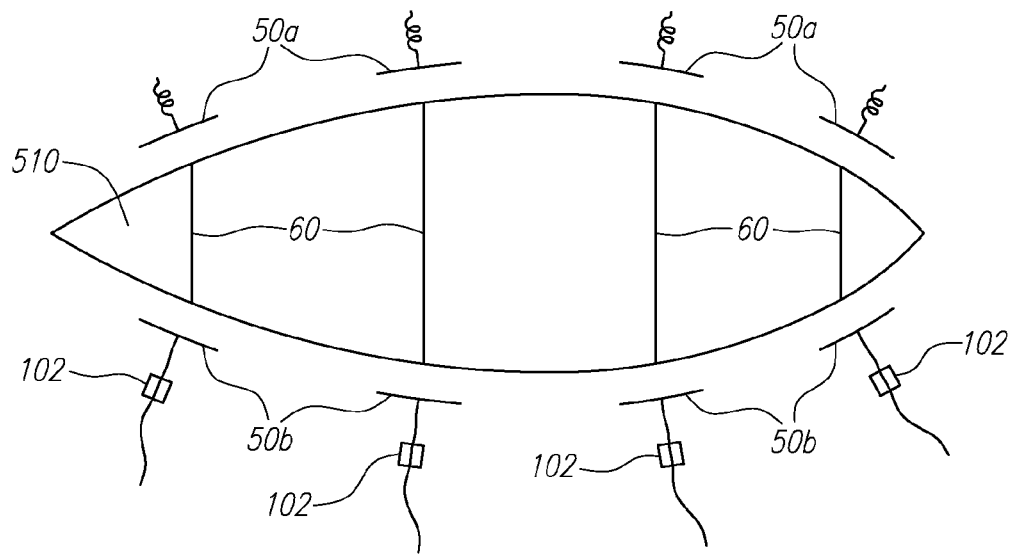
FIGS. 27A-D are illustrations showing several stages of an incisional hernia repair as viewed, for example, through a laparoscope located in the peritoneum of the patient and directed toward the hernia defect.
Figure 27B:
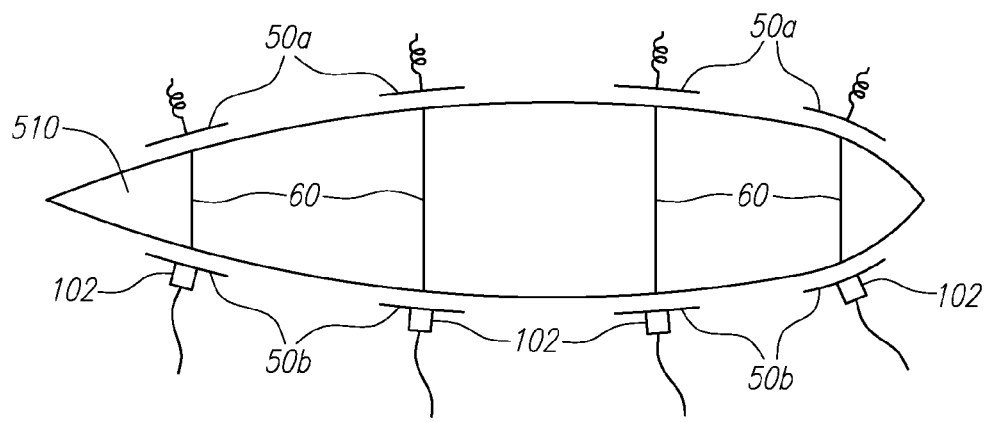

FIGS. 27A-D show a plurality of four tissue anchor assemblies 100 deployed through fascia tissue 512 on opposed sides of a hernia defect 510. The view shown in the illustration provided by FIGS. 27A-D is that which would be provided by a laparoscope viewing the hernia defect 510 from inside the peritoneal space during the repair procedure. Each of the tissue anchor assemblies 100 includes first and second tissue anchors 50a, 50b attached to each other by a suture 60, and having a uni-directional cinch 102 slidable on the suture 60 outside the second tissue anchor 50b. The span of the suture 60 is sufficient to extend across the widest portion of the hernia defect prior to approximation. In some embodiments, the suture span is at least about 15 cm. In other embodiments, the suture span is at least about 10 cm. In still other embodiments, the suture span is at least about 5 cm. In FIG. 27A, each of the four tissue anchor assemblies 100 has been deployed across the defect 510 without approximating the respective first and second tissue anchors 50a, 50b. In some embodiments, each of the tissue anchor assemblies 100 is partially approximated, as shown in FIG. 27B, in order to partially approximate the fascia edges 512a, 512b. In an embodiment, the tissue anchor assemblies 100 are partially approximated one at a time beginning at one end of the defect 510 and working toward the other end of the defect 510, such that the approximating forces may be substantially evenly distributed between each of the tissue anchor assemblies 100. The partial approximation of each of the tissue anchor assemblies 100 is repeated until all of the tissue anchor assemblies 100 are approximated by the desired amount, such as the substantially fully approximated orientation shown in FIG. 27C.

Figure 27C:
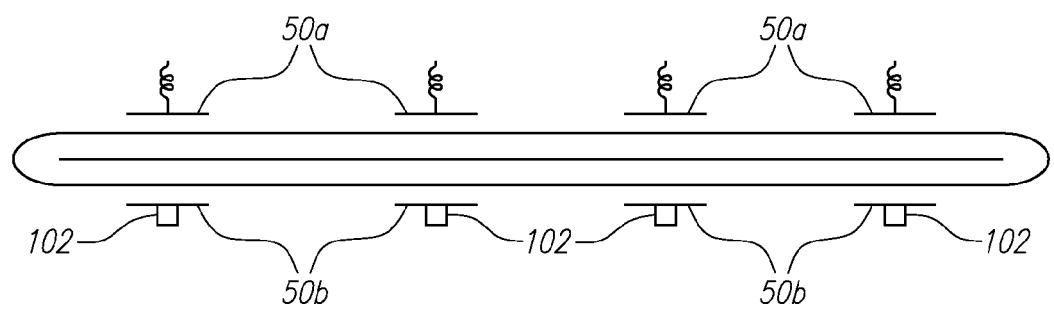

In the embodiments shown in FIGS. 27A-C, the tissue anchor assemblies 100 include sutures 60 aligned in parallel adjacent to one another. In other embodiments, the tissue anchors 50a, 50b of one or more of the tissue anchor assemblies 100 are deployed such that the sutures 60 cross over one another. The alignment of the sutures 60 of the tissue anchor assemblies 100 is generally at the discretion of the surgeon or other user.

Figure 27D:
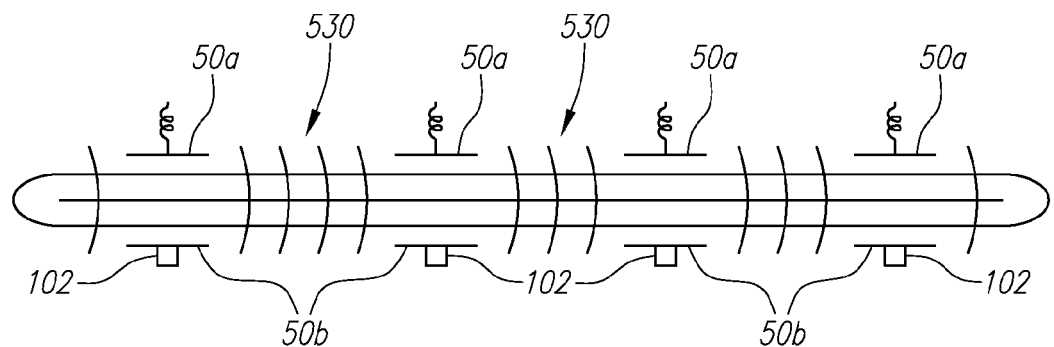

As discussed above, in some embodiments, a suture 530 is used to oversew the approximated defect 510, as shown in FIG. 27D. In the embodiment shown in FIG. 27D, a running stitch of suture 530 is used to oversew the approximated defect 510. (Note that the oversew stitches are not shown over the tissue anchors 50a, 50b for clarity). Those skilled in the art will recognize that other suturing methods may be used to provide the oversew support, as desired.

Turning next to FIGS. 28A-E, another embodiment of a laparoscopic hernia repair method is shown. As shown in FIG. 28A, a tissue manipulation end effector 214 of a tissue anchor deployment device having a curved or steerable distal region is inserted through a trocar and into the peritoneal space, and is brought into the vicinity of the hernia defect 510 and, more particularly, into the vicinity of the edges of the fascia 512a, 512b surrounding the hernia defect 510. As described more fully above, the exemplary tissue anchor deployment device described herein includes a needle deployment assembly 260, the distal end of which is translatably located within the launch tube 228 portion of the tissue anchor deployment device. In the embodiment shown, the jaws 220, 222 of the tissue manipulation end effector 214 are used to grasp a second one of the edges of the fascia 512b surrounding the hernia defect 510. After the second fascia edge 512b is engaged, the second anchor 50b (or other fastener) and cinch 102 (or other locking mechanism) are then deployed from the device via the needle deployment assembly 260 through the grasped region of the fascia 512b, as shown in FIG. 28B. In the embodiment shown, the second fascia edge 512a is grasped by the jaws 220, 222 of the end effector 214 such that the second anchor 50b and cinch 102 are deployed on the peritoneal side of the second fascia edge 512b. With proper positioning of the laparoscope, the needle 272 of the needle deployment assembly 260 is deployed under full visualization of the needle 272 as it advances from the distal end of the launch tube 228, through the fascia edge 512b, and into the space of the peritoneal cavity.

The second fascia edge 512b is then released, and the end effector 214 is repositioned to grasp a first of the edges of the fascia 512a located substantially opposite to the second fascia edge 512b across the hernia defect 510. Advantageously, because of the curved distal region 212b and/or the steerability of the distal region 212b of the tubular body 212, the orientation of the distal end effector 214 relative to the tubular body 212 of the device is such that the device need only be advanced distally, where it is in position to engage the first fascia edge 512a. The suture 60 of the tissue anchor assembly 100 extends out of the needle deployment assembly 260 located within the launch tube 228 of the device, through the first fascia edge 512a, and through the second tissue anchor 50b. As shown in FIG. 28C, the needle deployment assembly 260 is then advanced through the first fascia edge 512a, where the first tissue anchor 50a is deployed. In the embodiment shown, the first fascia edge 512a is grasped by the jaws 220, 222 of the end effector 214 such that the first anchor 50a is deployed on the abdominal side of the first fascia edge 512a.

Turning next to FIG. 28D, the anchor assembly 100 is then released from the deployment device 208, leaving the anchor assembly 100 spanning the hernia defect 510. The cinch 102 (or other locking mechanism) is then advanced over the suture 60 in order to approximate the distal and proximal anchors 50a, 50b, thereby approximating the edges of the fascia 512a, 512b in the overlapping orientation shown in FIG. 28E. As discussed above, in several embodiments, a plurality of additional tissue anchor assemblies 100 are deployed adjacent to one another along the length of the hernia defect 510. Turning to FIG. 25A, after the first and second tissue anchors 50a, 50b of each of the plurality of tissue anchor assemblies 100 have been deployed through the first fascia edge 512a and second fascia edge 512b, the unidirectional cinch 102 of each tissue anchor assembly 100 is advanced over the suture 60 to thereby cause the tissue anchors 50a, 50b to be approximated and to cause the first fascia edge 512a to be brought into proximity to the second fascia edge 512b.

Figure 29A:
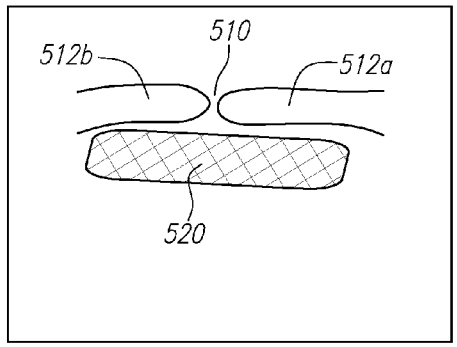
FIGS. 29A-E are cross-sectional views showing the progression of a portion of a laparoscopic hernia repair procedure.
Figure 29B:
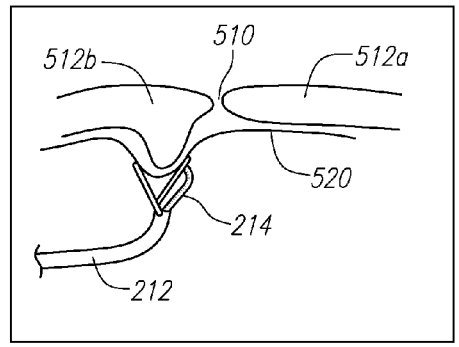
Figure 29C:
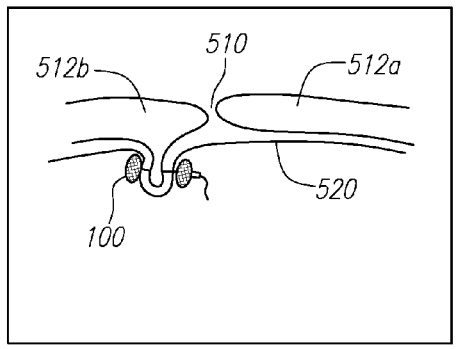
Figure 29D:
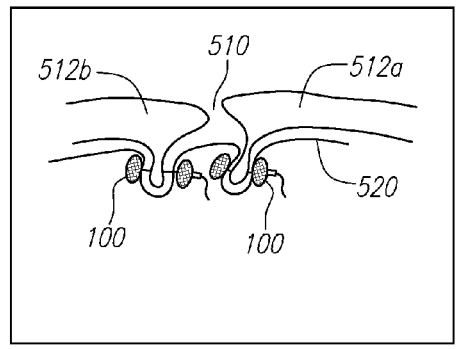
Figure 29E:
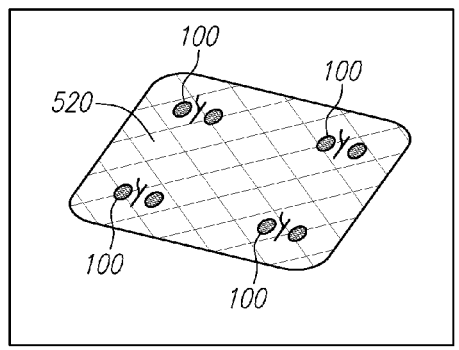

Another alternative embodiment of a laparoscopic hernia repair method is shown in FIGS. 29A-E. In the alternative method, a surgical mesh 520 is first placed over the hernia defect 510 in the manner shown in FIG. 29A. Once the surgical mesh 520 is in place, a tissue anchor deployment device is advanced into the vicinity of the hernia defect 510, as shown in FIG. 29B. A first tissue fold is then formed in tissue, such as at one edge of the fascia 512b surrounding the hernia defect, and a first tissue anchor assembly 100 is deployed through the tissue fold and through at least a portion of the surgical mesh 520. (See FIG. 29C). In this manner, the surgical mesh 520 is attached to the tissue fold and/or the tissue surrounding the hernia defect 510 via the tissue anchor assembly 100. Next, a second tissue fold is formed in the tissue, such as the tissue on or near another edge of the fascia 512a, and a second tissue anchor assembly 100 is deployed through the second tissue fold and through the surgical mesh 520, as shown in FIG. 29D. In some embodiments, the tissue anchor assemblies 100 are attached such that a tension force is maintained through the surgical mesh 520 to thereby partially or fully approximate the fascia edges 512a, 512b, thereby partially or fully closing the hernia defect 510. In other embodiments, the tissue anchor assemblies 100 are attached without creating a tension force carried by the surgical mesh 520, in which case the tissue anchor assemblies 100 serve to secure the surgical mesh 520 to the tissue. Additional tissue anchor assemblies 100 may be deployed in a similar manner as determined by the surgeon or other clinician. The tissue anchor assemblies 100 thereby secure the surgical mesh 520 to the tissue surrounding the hernia defect in a manner such that the surgical mesh 520 substantially or completely covers the hernia defect. (See FIG. 29E).

Figure 30A:
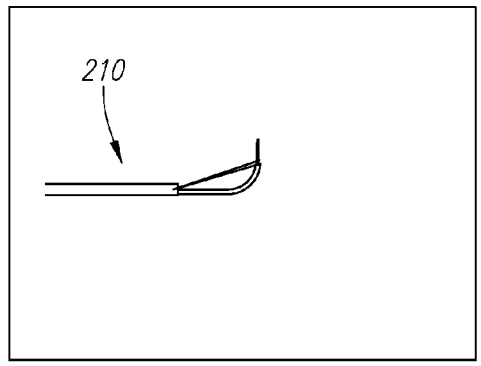
FIGS. 30A-E are cross-sectional views showing the progression of a portion of a laparoscopic hernia repair procedure.
Figure 30B:
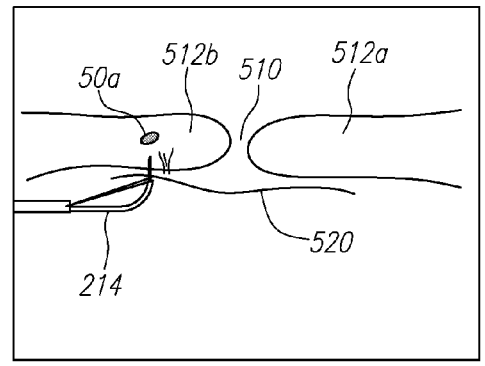
Figure 30C:
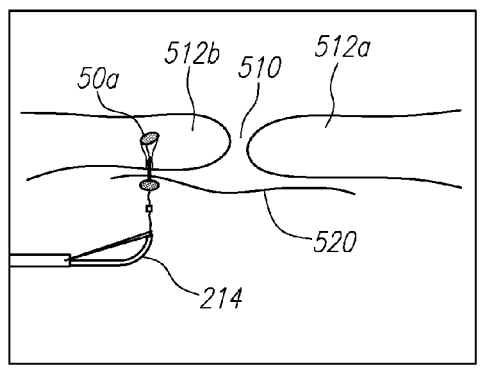
Figure 30D:
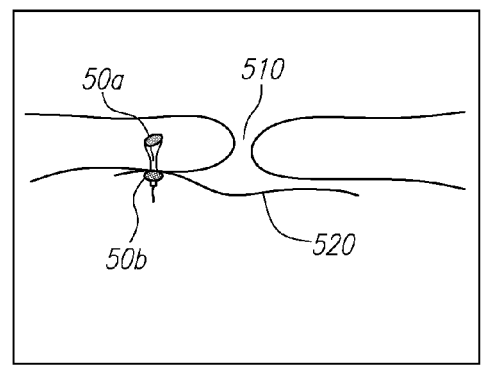
Figure 30E:
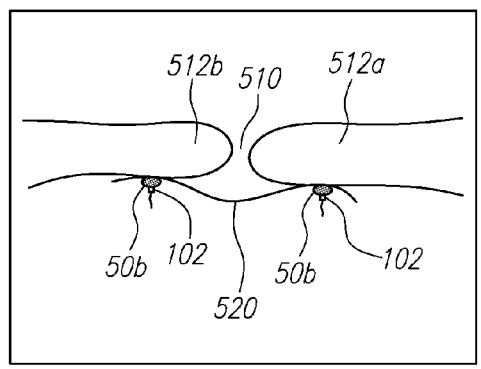

Turning to FIGS. 30A-E, still another alternative embodiment of a laparoscopic hernia repair method is shown. In the embodiment shown, a modified tissue manipulation device 210 is provided having only an upper jaw member 222, which may be attached to the tubular body 212 via a manifold 219. (See FIG. 30A). The modified device 210 is actuated by applying a distally-directed force upon the launch/drive tube 228 via the handle 216, which causes the distal region of the launch tube 228 to form the arcuate shape shown in FIG. 30A. This creates a passage for deploying a tissue anchor assembly 100 or other fastener via a needle deployment assembly 260. Accordingly, as shown in FIG. 30B, the distal end effector 214 of the modified device is brought into the vicinity of a fascia edge 512b surrounding a hernia defect 510. A first tissue anchor 50a is deployed by the modified device 210 through a surgical mesh 520 and either through or, as shown in FIG. 30B, into the fascia tissue 512b. The needle assembly 260 is then retracted from the tissue and the surgical mesh 520 and the second tissue anchor 50b and locking mechanism 102 of the tissue anchor assembly 100 are deployed and secured. (See FIGS. 30C and 30D). The tissue anchor assembly 100 thus deployed secures the surgical mesh 520 to the fascia tissue 512b. One or more additional tissue anchor assemblies are then optionally deployed at additional locations of fascia tissue 512a surrounding the hernia defect 510, further securing the mesh 520 to the tissue. In the embodiment shown, the surgical mesh 520 is thereby secured to the fascia tissue and substantially or completely covers the hernia defect 510.

The described methods include several embodiments, including all of the embodiments described herein as well as all combinations of each of those embodiments. Additional combinations of the therapeutic methods described herein will obtain similar results. In addition, other versions of the foregoing methods have been contemplated and are within the scope of the present methods. For example, the devices and methods may be incorporated into methods for repairing tissue defects and/or approximating regions of tissue in open surgical procedures, endolumenal surgical procedures, and other surgical or diagnostic procedures. As a specific example, the devices and methods may be used to approximate opposed regions of tissue in the vicinity of a hernia defect in an open surgical procedure.

Although various illustrative embodiments are described above, it will be evident to one skilled in the art that various changes and modifications are within the scope of the invention. It is intended in the appended claims to cover all such changes and modifications that fall within the true spirit and scope of the invention.

What is claimed is:

1. A method for laparoscopically repairing a hernia defect in a patient, comprising:
    grasping a first region of tissue on a first side of the hernia defect with a laparoscopic tool;
    piercing through the grasped first region of tissue with a needle;
    deploying a first tissue anchor from the needle;
    withdrawing the needle from the first region of tissue;
    grasping a second region of tissue on a second side of the hernia defect with the laparoscopic tool;
    piercing through the grasped second region of tissue with the needle;
    deploying a second tissue anchor from the needle, with the second tissue anchor connected to the first tissue anchor via a suture;
    withdrawing the needle from the second region of tissue;
    tensioning the suture and moving the first and second tissue anchors towards each other to draw the first and second regions of tissue towards each other; and
    sliding a locking mechanism along the suture to prevent the tissue anchors from moving away from each other.

2. The method of claim 1 further comprising deploying a plurality of additional tissue anchors into or through the first and second regions of tissue.

3. The method of claim 1 wherein said second tissue anchor is located on the suture between the first tissue anchor and the locking mechanism, and wherein the locking mechanism and second tissue anchor are slidably retained on the suture.

4. The method of claim 3 wherein the locking mechanism comprises a cinch that is slidable on the suture in only a single direction.

5. The method of claim 1 further comprising moving the first and second tissue anchors towards each other by pulling on the suture and pushing the second anchor towards the first anchor.

6. The method of claim 1 further comprising applying a surgical mesh over the first and second regions of tissue and securing the surgical mesh to the tissue.

7. The method of claim 1 further including positioning surgical mesh over the hernia defect and with the piercing steps including piercing through the surgical mesh.

8. A method for laparoscopically repairing a hernia defect in a patient, comprising:
    grasping a first region of tissue on a first side of the hernia defect with a first laparoscopic tool;
    piercing through the grasped first region of tissue with a needle;
    deploying a first tissue anchor from the needle;
    withdrawing the needle from the first region of tissue;
    grasping a second region of tissue on a second side of the hernia defect with a second laparoscopic tool;
    piercing through the grasped second region of tissue with the needle;
    deploying a second tissue anchor from the needle, with the second tissue anchor connected to the first tissue anchor via a suture;
    withdrawing the needle from the second region of tissue;
    tensioning the suture and moving the first and second tissue anchors towards each other to draw the first and second regions of tissue towards each other; and
    sliding a locking mechanism along the suture to prevent the tissue anchors from moving away from each other.

9. The method of claim 8 further including positioning surgical mesh over the hernia defect and with the piercing steps including piercing through the surgical mesh.

10. A method for laparoscopically repairing a hernia defect in a patient, comprising:
    grasping a first region of tissue on a first side of the hernia defect;
    piercing through the grasped first region of tissue with a needle;
    deploying a first tissue anchor from the needle;
    withdrawing the needle from the first region of tissue;
    grasping a second region of tissue on a second side of the hernia defect;
    piercing through the grasped second region of tissue with the needle;
    deploying a second tissue anchor from the needle, with the second tissue anchor connected to the first tissue anchor via a suture;
    withdrawing the needle from the second region of tissue;
    tensioning the suture and moving the first and second tissue anchors towards each other to draw the first and second regions of tissue towards each other; and
    sliding a locking mechanism along the suture to prevent the tissue anchors from moving away from each other.

11. The method of claim 10 further including positioning surgical mesh over the hernia defect and with the piercing steps including piercing through the surgical mesh.

* * * * *